US010905738B2

(12) United States Patent
França do Nascimento et al.

(10) Patent No.: US 10,905,738 B2
(45) Date of Patent: Feb. 2, 2021

(54) SYNTHETIC PEPTIDES, PRODRUGS, PHARMACEUTICAL COMPOSITIONS AND USES

(71) Applicant: Biozeus Desenvolvimento De Produtos Biofarmacêuticos, Rio de Janeiro (BR)

(72) Inventors: Caio Victor Machado França do Nascimento, Rio de Janeiro (BR); Diego Allonso Rodrigues dos Santos da Silva, Rio de Janeiro (BR); Perla Villani Borges da Silva, Rio de Janeiro (BR); Maria Elena De Lima Perez Garcia, Belo Horizonte (BR); Carolina Nunes da Silva, Belo Horizonte (BR); Adriano Monteiro de Castro Pimenta, Lagoa Santa (BR); Marcella Nunes de Melo Braga, Belo Horizonte (BR); Paulo Gustavo Sampaio Lacativa, Rio de Janeiro (BR); Iron Francisco de Paula Junior, Tijuca (BR); Gerhard Max Gross, Guaratinguetä (BR)

(73) Assignee: Biozeus Desenvolvimento De Produtos Biofarmacêuticos, Rio de Janeiro (BR)

( * ) Notice: Subject to any disclaimer, the term of this patent is extended or adjusted under 35 U.S.C. 154(b) by 0 days.

(21) Appl. No.: 16/502,215

(22) Filed: Jul. 3, 2019

(65) Prior Publication Data
US 2020/0108118 A1 Apr. 9, 2020

Related U.S. Application Data

(60) Provisional application No. 62/694,162, filed on Jul. 5, 2018.

(51) Int. Cl.
| | | |
|---|---|---|
| *A61K 38/10* | (2006.01) | |
| *A61K 38/08* | (2019.01) | |
| *A61K 38/16* | (2006.01) | |
| *A61K 47/55* | (2017.01) | |
| *C07K 7/08* | (2006.01) | |
| *C07K 7/06* | (2006.01) | |
| *C07K 14/00* | (2006.01) | |
| *A61P 11/06* | (2006.01) | |
| *A61P 11/08* | (2006.01) | |
| *A61P 15/10* | (2006.01) | |
| *A61P 35/00* | (2006.01) | |
| *A61P 9/12* | (2006.01) | |
| *A61K 47/64* | (2017.01) | |

(52) U.S. Cl.
CPC ............ *A61K 38/10* (2013.01); *A61K 47/643* (2017.08); *A61P 9/12* (2018.01)

(58) Field of Classification Search
CPC ........ A61K 38/10; A61K 38/08; A61K 38/16; A61K 47/643; A61K 47/55; C07K 7/08; C07K 7/10; C07K 14/00; C07K 2319/00; C07K 7/06; A61P 11/06; A61P 11/08; A61P 15/10; A61P 35/00; A61P 9/12
USPC ....... 530/300, 324, 325, 326, 327, 328, 329, 530/330; 514/1.1, 21.3, 21.4, 21.5, 21.6, 514/21.7, 21.8, 15.7
See application file for complete search history.

(56) References Cited

U.S. PATENT DOCUMENTS

| | | | |
|---|---|---|---|
| 8,715,688 B2 | 5/2014 | Meinke et al. | |
| 9,279,004 B2* | 3/2016 | De Lima Perez Garcia | ............... A61P 15/00 |
| 9,879,060 B2 | 1/2018 | Lee et al. | |
| 2011/0236467 A1 | 9/2011 | Perez Garcia et al. | |
| 2015/0218233 A1* | 8/2015 | De Lima Perez Garcia | ............... A61K 38/10 424/450 |

FOREIGN PATENT DOCUMENTS

| | | |
|---|---|---|
| EP | 3339319 A1 | 6/2018 |
| WO | 2014028997 A1 | 2/2014 |
| WO | 2017068388 A2 | 4/2017 |

OTHER PUBLICATIONS

P29425 from UniProt, pp. 1-7. Integrated into UniProtKB/Swiss-Prot on Apr. 1, 1993. (Year: 1993).*
A7N4M4 from UniProt, pp. 1-3. Integrated into UniProtKB/TrEMBL on Oct. 2, 2007. (Year: 2007).*
Carolina Nunes Silva et al., "PnPP-19, a synthetic and nontoxic peptide designed from a Phoneutria nigriventer toxin, potentiates erectile function via NO/cGMP" The Journal of Urology, Jun. 2015, pp. 1481-1490, vol. 194, Issue 5.

(Continued)

*Primary Examiner* — Julie Ha
(74) *Attorney, Agent, or Firm* — Pilloff Passino & Cosenza LLP; Sean A. Passino; Rachel K. Pilloff

(57) ABSTRACT

Synthetic peptides that are modulators of smooth muscle tone and compositions thereof, including pharmaceutical compositions containing a peptide, make it possible to treat indications in those in need of modulation of the smooth muscle tone, including, for example, benign prostate hyperplasia (BPH), Raynaud's syndrome, Pulmonary Arterial hypertension (PAH), systemic arterial hypertension (SAH) and hyper-reactivity of airways associated with asthma, COPD, pulmonary fibrosis, silicosis, allergic bronchopulmonary aspergillosis, hereditary angioedema, and neonatal hypoxemic respiratory failure. Although makeable in other ways, the synthetic peptides are makeable by recombinant methods or synthetic pathways.

15 Claims, 5 Drawing Sheets
Specification includes a Sequence Listing.

(56) References Cited

OTHER PUBLICATIONS

Zhibo Liu et al., "Simple bioconjugate chemistry serves great clinical advances: albumin as a versatile platform for diagnosis and precision therapy," Chem Soc Rev., Mar. 2016, pp. 1432-1456, vol. 45, No. 5.
International Search Report & Written Opinion for PCT/BR2019/050249, dated Sep. 30, 2019.
Alessandra Matavel et al., "Structure and Activity Analysis of Two Spider Toxins That Alter Sodium Channel Inactivation Kinetics," Biochemistry, Feb. 2009, pp. 3078-3088, vol. 48, No. 14.
Flavia De Marco Almeida et al., "Physicochemical Characterization and Skin Permeation of Cationic Transfersomes Containing the Synthetic Peptide PnPP-19," Current Drug Delivery, Jan. 2018, pp. 1064-1071, vol. 15, No. 17.

\* cited by examiner

SEQUENCE LISTING

<160> NUMBER OF SEQ ID NOS: 30

<210> SEQ ID NO 1
<211> LENGTH: 15

-continued

```
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 1

Arg Ala Tyr Phe Trp Ile Ala Trp Tyr Lys Leu Ala Asn Ser Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 2

Arg Gln Tyr Phe Trp Ile Ala Trp Tyr Lys Leu Ala Asn Ser Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 3

Arg Gln Ala Phe Trp Ile Ala Trp Tyr Lys Leu Ala Asn Ser Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 4

Ala Gln Tyr Phe Trp Ile Ala Trp Tyr Lys Leu Ala Asn Ser Lys
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 5
```

Arg Gln Tyr Phe Trp Ile Ala Trp Tyr Lys Leu Ala Asn Ser Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 6

Arg Gln Tyr Phe Trp Ile Ala Trp Tyr Lys Ile Ala Ser Asn Lys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: synthetic peptide
<220> FEATURE:
<223> OTHER INFORMATION: Synthetic PRT based around -Ile-Ala-Trp-

<400> SEQUENCE: 7

Arg Gln Tyr Phe Trp Ala Ala Trp Tyr Lys Leu Ala Asn Ser Lys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: synthetic peptide
<220> FEATURE:
<223> OTHER INFORMATION: Synthetic PRT based around -Ile-Ala-Trp-

<400> SEQUENCE: 8

Arg Gln Tyr Phe Trp Ile Ala Ala Tyr Lys Leu Ala Asn Ser Lys
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 9

Arg Gln Tyr Ala Trp Ile Ala Trp Tyr Lys Leu Ala Asn Ser Lys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

```
<400> SEQUENCE: 10

Arg Gln Tyr Phe Ala Ile Ala Trp Tyr Lys Leu Ala Asn Ser Lys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 11

Arg Gln Tyr Phe Trp Ile Ala Trp Ala Lys Leu Ala Asn Ser Lys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 12

Arg Gln Tyr Phe Trp Ile Ala Trp Tyr Ala Leu Ala Asn Ser Lys
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 13

Arg Gln Tyr Phe Trp Ile Ala Trp Tyr Lys Leu Ala Ala Ser Lys
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 14

Arg Gln Tyr Phe Trp Ile Ala Trp Tyr Lys Leu Ala Asn Ala Lys
1               5                   10                  15

<210> SEQ ID NO 15
<211> LENGTH: 15
<212> TYPE: PRT
<213> ORGANISM: Artificial Sequence
<220> FEATURE:
```

```
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 15

Glu Gln Tyr Phe Trp Ile Ala Trp Tyr Lys Ile Ala Asn Ser Lys
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 16

Arg Gln Tyr Phe Trp Ile Ala Trp Tyr Lys Ile Ala Asn Ser Glu
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (5)...(7)
<223> OTHER INFORMATION: Synthetic PRT based around -Ile-Ala-Trp-

<400> SEQUENCE: 17

Gln Tyr Phe Trp Ile Ala Trp Tyr Lys Leu Ala Asn Ser
1               5                   10

<210> SEQ ID NO 18
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (4)...(6)
<223> OTHER INFORMATION: Synthetic PRT based around -Ile-Ala-Trp-

<400> SEQUENCE: 18

Tyr Phe Trp Ile Ala Trp Tyr Lys Leu Ala Asn
1               5                   10

<210> SEQ ID NO 19
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (3)...(5)
<223> OTHER INFORMATION: Synthetic PRT based around -Ile-Ala-Trp-

<400> SEQUENCE: 19

Phe Trp Ile Ala Trp Tyr Lys Leu Ala
1               5
```

```
<210> SEQ ID NO 20
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 20

Arg Gln Tyr Phe Trp Ile Ala Trp Tyr
1               5

<210> SEQ ID NO 21
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (3)...(5)
<223> OTHER INFORMATION: Synthetic PRT based around -Ile-Ala-Trp-

<400> SEQUENCE: 21

Tyr Trp Ile Ala Trp Tyr Lys Leu Leu
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (6)...(8)
<223> OTHER INFORMATION: Synthetic PRT based around -Ile-Ala-Trp-

<400> SEQUENCE: 22

Arg Gln Tyr Phe Trp Ile Ala Trp
1               5

<210> SEQ ID NO 23
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (2)...(4)
<223> OTHER INFORMATION: Synthetic PRT based around -Ile-Ala-Trp-

<400> SEQUENCE: 23

Trp Ile Ala Trp Tyr Lys Leu
1               5

<210> SEQ ID NO 24
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)...(3)
<223> OTHER INFORMATION: Synthetic PRT based around -Ile-Ala-Trp-
```

```
<400> SEQUENCE: 24

Ile Ala Trp Tyr Lys
1               5

<210> SEQ ID NO 25
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)...(3)
<223> OTHER INFORMATION: Synthetic PRT based around -Ile-Ala-Trp-

<400> SEQUENCE: 25

Ile Ala Trp Tyr Glu
1               5

<210> SEQ ID NO 26
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)...(3)
<223> OTHER INFORMATION: Synthetic PRT based around -Ile-Ala-Trp-

<400> SEQUENCE: 26

Ile Ala Tyr Tyr Lys
1               5

<210> SEQ ID NO 27
<211> LENGTH: 18
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (9)...(11)
<223> OTHER INFORMATION: Synthetic PRT based around -Ile-Ala-Trp-

<400> SEQUENCE: 27

Gly Glu Arg Arg Gln Tyr Phe Trp Ile Ala Trp Tyr Lys Leu Ala Asn
1               5                   10                  15

Ser Lys

<210> SEQ ID NO 28
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)...(3) AND (11)...(13)
<223> OTHER INFORMATION: synthetic PRT based around -Ile-Ala-Trp-
<220> FEATURE:
<221> NAME/KEY: misc_feature
<222> LOCATION: (6)...(10)
<223> OTHER INFORMATION: amino acid is optionally linked to poly-Gly
      linkers

<400> SEQUENCE: 28

Ile Ala Trp Tyr Lys Gly Gly Gly Gly Gly Ile Ala Trp Tyr Lys
```

```
                1               5              10              15

<210> SEQ ID NO 29
<211> LENGTH: 17
<212> TYPE: PRT
<213> ORGANISM: Artificial Sequence
<220> FEATURE:
<221> NAME/KEY: misc_feature
<222> LOCATION: (1)...(3)
<223> OTHER INFORMATION: synthetic PRT based around -Ile-Ala-Trp-
<220> FEATURE:
<223> OTHER INFORMATION: synthetic peptide
<220> FEATURE:
<221> NAME/KEY: misc_feature
<222> LOCATION: (7)...(11)
<223> OTHER INFORMATION: amino acid is optionally linked to poly-Gly
      linkers

<400> SEQUENCE: 29

Ile Ala Trp Tyr Lys Arg Gly Gly Gly Gly Arg Lys Tyr Trp Ala
1               5                  10                  15

Ile

<210> SEQ ID NO 30
<211> LENGTH: 25
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)...(3) AND (11)...(13) AND (21)...(23)
<223> OTHER INFORMATION: synthetic PRT based around -Ile-Ala-Trp-
<220> FEATURE:
<221> NAME/KEY: misc_feature
<222> LOCATION: (6)...(10) AND (16)...(20)
<223> OTHER INFORMATION: amino acid is optionally linked to poly-Gly
      linkers

<400> SEQUENCE: 30

Ile Ala Trp Tyr Lys Gly Gly Gly Gly Gly Ile Ala Trp Tyr Lys Gly
1               5                  10                  15

Gly Gly Gly Gly Ile Ala Trp Tyr Lys
                20                  25
```

SYNTHETIC PEPTIDES, PRODRUGS, PHARMACEUTICAL COMPOSITIONS AND USES

CROSS REFERENCE

The present application claims priority benefit of U.S. Application No. 62/694,162, filed 5 Jul. 2018, the contents of which are incorporated herein by reference.

TECHNICAL FIELD

The present invention refers to synthetic peptides that are modulators of smooth muscle tone and compositions thereof. It also refers to pharmaceutical compositions containing such peptides and the uses thereof in the treatment in which the modulation of the smooth muscle tone is beneficial.

BACKGROUND

The smooth muscle tissue is an important structural component and regulator of the function of various organs and systems. Smooth muscle contractility disorders are associated with a range of clinical manifestations, particularly diseases of the respiratory, vascular, genitourinary and gastrointestinal tracts.

Different mechanisms control the tone of smooth muscles in response to either local or systemic stimuli. Mediators produced by adjacent structures, such as, for example, the Nitric Oxide (NO) fine-tune the tone at the local level. Complementarily, the action of the Autonomous Nervous System (ANS), either through sympathetic or parasympathetic fibers, regulates the contractility of the smooth muscles in response to stimuli perceived and processed by the Central Nervous System (CNS). However, neurotransmitter receptors are expressed differentially in the smooth muscle tissue depending on the macrostructure in which such cells are inserted. Therefore, the pharmacological control of the smooth muscle tone differs significantly in diseases of the respiratory, vascular and genitourinary systems. Pharmacological approaches may even produce opposed effects (i.e. contraction vs. relaxing) in different systems.

Smooth muscle cells are in the walls of all blood vessels with the exception of capillary vessels and pericytic venules. Whenever present, the smooth muscles are the main regulator of the vascular distensibility, and therefore of the diameter of the vessels. Thus, the variation in the tone of the smooth muscles determines the vascular diameter, greatly influencing the peripheral resistance and consequently the blood flow. In pathological conditions, the vascular smooth muscles are related to the development and progression of arterial hypertension, and therefore they are also targeted by therapeutic approaches that reduce the resistance to the blood flow. The pharmacological classes employed for such purpose include sympathetic ANS stimuli blockers (adrenergic antagonists), angiotensin converter inhibitors or NO donor vasodilators.

Similarly, the corpus cavernosum—vascular structures directly involved in the intumescence of the penis—are also constituted by a layer of smooth muscle tissue. The erection is a neurovascular event that depends on the integrity of the vascular, muscular and nervous substructures that constitute the penis. When stimulated, the nervous terminations adjacent to the cavernous bodies and the endothelial cells coating those vessels release NO. The subsequent signaling cascade results in the relaxation of the cavernosal smooth muscle increase of the blood flow into those structures, and finally, the erection. Failures in that mechanism may result in an impaired erection, insufficient for sexual intercourse, characterizing the erectile dysfunction (ED).

The therapy for reversal of ED aims at the relaxation of the cavernosal smooth muscles and subsequent increase of blood flow inside the corpus cavernosum. In this regard, Phosphodiesterase-5 inhibitors (PDE5i) comprise the first line of treatment. However, 36% of the patients are overtly resistant or intolerant to the PDE5i and must use other pharmacological options. In general, the alternative therapies have limited effectiveness and are inconvenient both in terms of administration (i.e. intraurethral or intracavernosal) and adverse effects, thus associated with high rates of discontinuation. However, both gold standard and second lines of treatment promote the increase of blood flow into the corpus cavernosum by relaxing the cavernosal smooth muscles. Therefore, there is an unmet medical need for drugs that are capable of producing the same effect, in a more convenient manner.

In the respiratory tract, smooth muscle cells integrate the upper airways and the entire tracheobronchial tree, actively regulating the caliber of these structures and consequently the airflow. The smooth muscle tone in a physiological situation is also regulated by local mediators and by the ANS. However, contrary to what occurs, for example, in the corpus cavernosum, the sympathetic signals promote the relaxation and increase of caliber of the airways. Also, in this case, the pharmacology of the adrenergic and cholinergic pathways is the basis for the modulation of contractility of the airways in pathological situations.

The smooth muscle tissue is a central effector of the bronchoconstriction associated with the airway hyperresponsiveness in which is a feature of inflammatory diseases of the respiratory tract. In these situations, it is common to observe hyperplasia and hypertrophy of the smooth muscle layer, which contributes to the thickening and increased airway contractility. B2-adrenergic agonists integrate the standard treatment for the rescue of acute bronchoconstriction in patients with asthma or chronic obstructive pulmonary disease (COPD). This therapeutic approach is particularly effective on account of the capacity to prevent contraction and induce relaxation of the smooth muscle in the airways. Following the same principle of reduction of contractility, muscarinic antagonists and phosphodiesterase 4 inhibitors (PDE4i) serve as the second and third line of treatment, particularly against exacerbations associated with COPD.

The peptides described here are capable of relaxing the smooth muscle of different anatomical structures, and therefore have a pleiotropic mechanism of action. Therefore, they are useful in the treatment of diseases that involve smooth muscle disorders in the vascular, gastrointestinal, respiratory and genitourinary tracts.

The technical-scientific literature comprises reports on peptides with a biological activity that is similar to those described herein. For example, the toxin of the spider *Phoneutria nigriventer* [South American Banana Spider], commonly known as Brazilian wandering spider is rich in bioactive polypeptides with different pharmacological effects. Among the symptoms provoked by the sting, the priapism observed in male victims raised interest from the pharmacological point of view. Patent application No. PI 0800596, filed in Brazil in 2008, described the effect of PnTx2-6 in the erectile function of rats. The therapeutic potential of the toxin PnTx-6 in the treatment of the erectile dysfunction is also described by the family of patents derived from CN101585872.

Subsequently, it was demonstrated that PnTx2-6 also restores the erectile function in hypertensive animals (DOCA-sal) and in diabetic mice or aged rats (for revision, see: NUNES, K. P. CARDOSO, F. L, CARDOSO-Jr., H. C, PIMENTA, A. M. C, De LIMA, M. E. Animal toxins as potential pharmacological tools for treatment of erectile dysfunction. In: Animal Toxin: State of the Art. Perspectives in Health and Biotechnology. Maria Elena de Lima, Adriano Monteiro de Castro Pimenta, Marie France Martin-Eauclaire, Russolina Benedeta Zingali and Hervë Rochat (editors), 759p., 2009; NUNES, K. P., COSTA-GONÇALVES, A., LANZA, L. F., CORTES, S. F., CORDEIRO, M. N., RICHARDSON, M., PIMENTA, A. M., WEBB, R. C., LEITE, R., DE LIMA, M. E. Tx2-6 toxin of the *Phoneutria nigriventer* spider potentiates rat erectile function. *Toxicon*, 51(7):197-206, 2008; ANTUNES, A. A., ISCAIFE, A., REIS, S. T., ALBERTINI, A., NUNES, M. A., LUCON, A. M., NAHAS, W. C., SROUGI, M. Can we predict which patients will experience resolution of detrusor overactivity after transurethral resection of the prostate? *The Journal of Urology*, 9 (10): 2574-81, 2012). These effects appear to be mediated by the activation of the enzyme Nitric Oxide Synthase (NOS) and the release of NO (YONAMINE, C. M., TRONCONE, L. R., CAMILLO, M. A. Blockade of neuronal nitric oxide synthase abolishes the toxic effects of Tx2-5, a lethal *Phoneutria nigriventer* spider toxin. *Toxicon*, 44, 169-172, 2004; NUNES, K. P., COSTA-GONÇALVES, A., LANZA, L. F., CORTES, S. F., CORDEIRO, M. N., RICHARDSON, M., PIMENTA, A. M., WEBB, R. C., LEITE, R., DE LIMA, M. E. Tx2-6 toxin of the *Phoneutria nigriventer* spider potentiates rat erectile function. *Toxicon*, 51 (7): 1 197-206, 2008, NUNES, K. P. CARDOSO, F. L, CARDOSO-Jr., H. C, PIMENTA, A. M. C, De LIMA, M. E. Animal toxins as potential pharmacological tools for treatment of erectile dysfunction. In: Animal Toxin: State of the Art. Perspectives in Health and Biotechnology. Maria Elena de Lima, Adriano Monteiro de Castro Pimenta, Marie France Martin-Eauclaire, Russolina Benedeta Zingali and Nerve Rochat (editors), 759p., 2009). Furthermore, it is suggested that some genes involved in the NO pathway have their expression enhanced in the erectile tissue of mice after treatment with the toxin PnTx2-6 (VILLANOVA F. E., ANDRADE E., LEAL E., ANDRADE, P. M., BORRA, R. C., TRONCONE, L. R., MAGALHAES, L., LEITE, K. R., PARANHOS, M., CLARO, J., SROUGI, M. Erection induced by Tx2-6 toxin of *Phoneutria nigriventer* spider: expression profile of genes in the nitric oxide pathway of penile tissue of mice. *Toxicon*. 54(6), 793-801, 2009.). U.S. Pat. No. 9,279,004 demonstrates the peptide PnTx(19), a derivative of 19 amino acids with a molecular weight of 2,485.85 Da, built from the toxin PnTx2-6. The disclosures reveal that the peptide is able to enhance the erectile function, as demonstrated by the induction of relaxation of murine cavernosal strips ex vivo. Later, Silva et al (SILVA, C. N., NUNES, K. P., TORRES, F. S., CASSOLI, J. S., SANTOS, D. M., ALMEIDA, Fde. M., MATAVEL, A., CRUZ, J. S., SANTOS-MIRANDA, A., NUNES, A. D., CASTRO, C. H., MACHADO D E AVILA, R. A., CHÁVEZ-OLÓRTEGUI, C., LÁUAR, S. S., FELICORI, L., RESENDE, J. M., CAMARGOS, E. R., BORGES, M. H., CORDEIRO, M. N., PEIGNEUR, S., TYTGAT, J., DE LIMA, M. E. PnPP19, a synthetic and nontoxic peptide designed from a *Phoneutria nigriventer* Toxin, potentiates erectile function via NO/cGMP. *J Urol;* 194(5): 1481-90. 2015) confirmed that the vasodilation promoted by PnTx (19) is mediated by the activation of NOS and production of NO, particularly by the neuronal and induced isoforms of NOS. Thus, PnTx(19) was claimed as a potential candidate for ED treatment, with the potential to be used in patients that are refractory to the therapy based on PDE5i.

The smooth muscle tone modulating peptides described in the present invention are more potent than those reported in the prior art. As an example, the peptides were evaluated comparatively to PnTx(19) in smooth muscle contractility experimental models already established in the scientific literature. As will be further shown, the smooth muscle modulator peptides show a significant activity wherein the comparator (PnTx(19)) is fully inactive (smooth muscle of airways) or has a clearly inferior activity (smooth muscle of penile corpus cavernosum). Moreover, PnTx(19) was shown to exert a proinflammatory effect in airway smooth muscle. Inflammation is an important part of the pathophysiology of many diseases, among those, pulmonary diseases like asthma and COPD, as a mechanism that provokes, or amplifies the worsening of said diseases. Therefore, the use of pro-inflammatory compounds is currently prohibited in such pulmonary diseases. The peptides described in the present invention are not pro-inflammatory acting instead in inhibiting inflammation in the pulmonary system. Furthermore, the effect of the peptides described herein is mediated by NO, a pleiotropic mechanism that increases the breadth of the potential therapeutic applications.

SUMMARY

In some embodiments, a peptide comprises a pharmacologically active peptide sequence of formula (2):
Xaa1-Xaa2-Xaa3-Xaa4-Xaa5-Ile-Ala-Trp-Xaa9-Xaa10-Xaa11-Xaa12-Xaa13-Xaa14-Xaa15 (2), the amino to carboxy direction being from left to right;
  wherein:
   each of Xaa1, Xaa2, and Xaa15 is independently absent or Ala, Arg, Lys or His;
   Xaa3 is independently absent or Ala, Phe, Trp or Tyr;
   each of Xaa4, Xaa5, and Xaa9 is independently absent or Phe, Trp or Tyr;
   Xaa10 is independently absent or His, Lys or Arg;
   Xaa11 is absent or Ala, Gly, Val, Leu, Ile, Pro, Cys or Met;
   Xaa12 is absent or Ala; and
   each of Xaa13 and Xaa14 is independently absent or Asn, Gln, Ser or Thr;
wherein the pharmacologically active peptide sequence of formula (2) has 5 or more contiguous amino acid residues.

In some embodiments, in formula (2), one or more amino acid residues of the group consisting of Xaa1, Xaa2, Xaa3, Xaa4, Xaa5, Xaa11, Xaa12, Xaa13, Xaa14, and Xaa15, are absent.

In some embodiments, the pharmacologically active peptide sequence of formula (2) is SEQ ID NO: 17, SEQ ID NO: 18, SEQ ID NO: 19, SEQ ID NO: 20, SEQ ID NO: 22, SEQ ID NO: 23, SEQ ID NO: 24 or SEQ NO ID: 5.

In some embodiments, the pharmacologically active peptide sequence of formula (2) has from 15 to 18 contiguous amino acid residues.

In some embodiments, the pharmacologically active peptide sequence of formula (2) has 18 contiguous amino acid residues.

In some embodiments, the peptide comprises at least a second peptide or protein.

In some embodiments, the peptide comprises a peptide of formula (1)

Z—X—Z'— (1)

in which:

X is the pharmacologically active peptide sequence of formula (2) as defined above; and each of Z and Z' is a peptide independently comprising a cell penetration-enhancing amino acid sequence or an activity-enhancing amino acid sequence having from 2 to 15 naturally-occurring amino acids.

In some embodiments, H, acetyl, chloride, or trifluoroacetyl is covalently bonded to the N-terminus of —Z—X—Z'—.

In some embodiments, OH or $NH_2$ is covalently bonded to the C-terminus of —Z—X—Z—.

In some embodiments, Z is a peptide comprising a sequence including, from N- to C-terminus, amino acid residues Gly, Glu, and Arg, respectively, has a pharmacologically active peptide sequence of SEQ ID NO: 5, and Z' is absent.

In some embodiments, any peptide above is linked to a half-life enhancing moiety selected from albumin-binding moieties. In some embodiments, the peptide is one in which the peptide has a N-terminus which is acetyl, and a C-terminus which is $NH_2$.

In some embodiments, the peptide, in the form of a multimer, comprises two or more peptides having a sequence of formula (2) interspaced by amino acid-based cleavable linkers, e.g., by esterification of the C-terminal domain, wherein the multimer is optionally N-terminally acylated and the C-terminally amidated.

In some embodiments, the invention comprises pharmaceutical compositions containing the smooth muscle tone modulating peptides and pharmaceutically acceptable vehicles, excipients or additives, useful for the treatment of diseases associated to the deregulation of contractility of the smooth muscles. For example, in some embodiments, a pharmaceutical composition, comprises one or more peptides defined above and a pharmaceutically acceptable excipient.

In some embodiments, the invention comprises the use of the smooth muscle tone modulating peptides for the treatment of diseases that benefit from the modulation of the smooth muscle contractility including, but not limited to: erectile dysfunction (ED), female sexual dysfunction (FSD), benign prostate hyperplasia (BPH), Raynaud's syndrome, Pulmonary Arterial hypertension (PAH), systemic arterial hypertension (SAH) and hyper-reactivity of airways associated with asthma, COPD, pulmonary fibrosis, silicosis, allergic bronchopulmonary aspergillosis, hereditary angioedema, and neonatal hypoxemic respiratory failure.

For example, a method of making a pharmaceutical composition, comprises introducing to a pharmaceutically acceptable excipient any one to more peptides above an amount sufficient to treatment of a disorder where the modulation of the tone of the smooth muscle is beneficial.

In some embodiments, the disorder is selected from the group consisting of erectile dysfunction (ED), female sexual dysfunction (FSD), benign prostatic hyperplasia (BPH), Raynaud's syndrome, pulmonary arterial hypertension (PAH), systemic arterial hypertension (SAH) and hyper-reactivity of airways related to asthma, COPD, pulmonary fibrosis, silicosis, allergic bronchopulmonary aspergillosis, hereditary angioedema, and neonatal hypoxemic respiratory failure.

In some embodiments, the peptide has an amino acid sequence of SEQ ID NO: 17, SEQ ID NO: 18, SEQ ID NO: 19, SEQ ID NO: 20, SEQ ID NO: 22, SEQ ID NO: 23, or SEQ ID NO: 24 and further wherein the disorder is PAH.

In some embodiments, a method for treating a disorder in a patient in need of modulation of the tone of smooth muscle, comprises administering to the patient a therapeutically effective amount of any one or more peptide above.

In some embodiments, the disorder is selected from the group consisting of erectile dysfunction (ED), female sexual dysfunction (FSD), benign prostatic hyperplasia (BPH), Raynaud's syndrome, pulmonary arterial hypertension (PAH), systemic arterial hypertension (SAH) and hyper-reactivity of the airways associated to asthma, COPD, pulmonary fibrosis, silicosis, allergic bronchopulmonary aspergillosis, hereditary angioedema, and neonatal hypoxemic respiratory failure.

In some embodiments, the peptide has an amino acid sequence of SEQ ID NO: 17, SEQ ID NO: 18, SEQ ID NO: 19, SEQ ID NO: 20, SEQ ID NO: 22 SEQ ID NO: 23, or SEQ ID NO: 24 and further wherein the disorder is PAH.

DESCRIPTION OF EMBODIMENTS

I—Definitions

Figure 1:
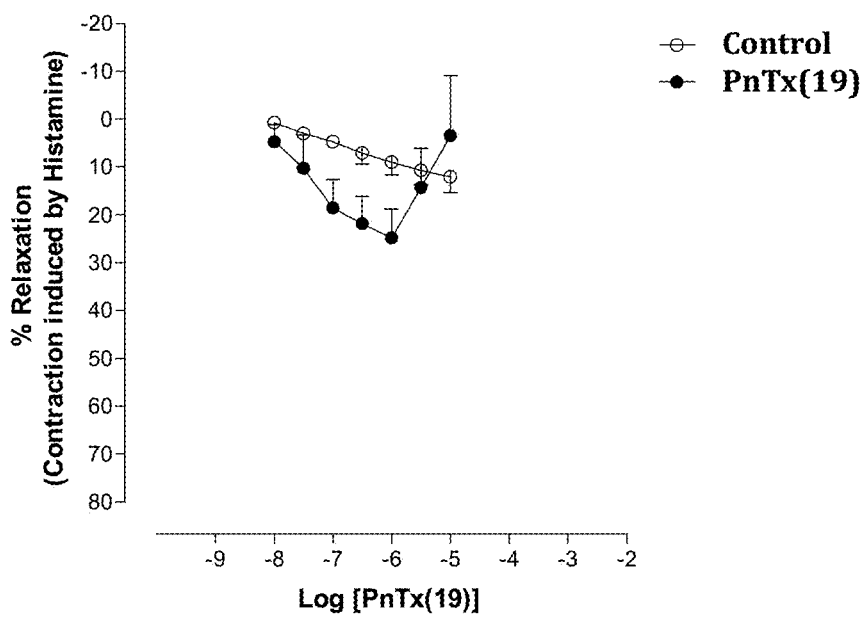
FIG. 1 shows the effect of PnTx(19) (0.01 to 10 μM), on the spasmodic contraction of tracheal rings induced by histamine ex vivo. The graph shows the mean±SEM of the results obtained with 8 tracheal rings from different animals.

Except if indicated otherwise, all the terms and expressions used herein have the same meaning that they would to a person skilled in the art of the present invention. Those skilled in the art are particularly directed to the reference "Current Protocols in Molecular Biology" for definitions and terms of the art (AUSUBEL, F. M., BRENT, R., KINGSTON, R. E., MOORE, D. D., SEIDMAN, G., SMITH, J. A., STRUHL, K. Current Protocols in Molecular Biology. John Wiley and Sons, Inc., Media Pa. 2015).

The abbreviations for amino acid residues are the standard code of 3 letters and/or 1 letter used in the art for reference to one of the common 20-L amino acids.

"Conservative amino acids substitutions" are substitutions that do not result in significant modification of the smooth muscle relaxant activity (for example, promotion activity of the relaxation of the smooth muscle) or tertiary structure of a given polypeptide or protein. Such substitutions typically involve the substitution of an amino acid residue selected by a different residue having similar physic-chemical properties. For example, the substitution of Glutamic Acid (Glu) with Aspartic acid (Asp) is deemed to constitute a conservative substitution, since they are both amino acids negatively charged of similar size. Grouping of amino acids by physical-chemical properties is known to those skilled in the art.

"Peptide" and "polypeptide" are used herein in an interchangeable form and refer to a compound constituted by a chain of amino acid residues linked by peptidic links. Unless indicated otherwise, the sequence of the peptides is given in the order of the amino-terminal to the carboxy-terminal.

The "identity" of a sequence is determined by comparing the sequence of amino acids of the polypeptides when aligned in order to maximize the superposition, minimizing the gaps of the sequence, followed by an accounting of identical residues between the sequences. The percentage of identity of two sequences of amino acids or nucleic acids can be determined by visual inspection and/or mathematical calculation, commonly done for longer sequences comparing the information of the sequence using a computer program. Examples of programs that can be used by a person skilled in the art for comparison of sequences of peptides and nucleic acids are the BLAST (BLASTP) and BLASTN, freely available in the website of the National Library of Medicine [ncbi.nlm.nih.gov/BLAST]. In preferred modalities, the sequences are considered homologous or identical to one another if their amino acid sequences are at least 50% identical, more preferably if the sequences are 70% or 75% identical, still more preferably if the sequences are 80% or 85% identical, still more preferably if the sequences are 90 or 95% identical, when determined from a visual inspection or an adequate computer program.

A peptide or a peptide fragment is "derived from" an original peptide or peptide fragment if there is a sequence of amino acids that is identical or homologous to the sequence of amino acids of the original peptide or polypeptide.

II—Smooth Muscle Relaxant Peptides and Compositions

In some embodiments, the present invention relates to synthetic peptides capable of promoting relaxation of the smooth muscles, particularly that which is present in airways and in vessels. Other peptides with similar activity are presented in the prior art, but none of the available reports either disclose or anticipates the compounds presented herein. The peptides in question are structurally unique and have a biological effect in systems that are not very sensitive or definitely insensible to other peptides thus may be deemed correlated thereto.

In some embodiments, a peptide comprises a pharmacologically active peptide sequence of formula (2):
Xaa1-Xaa2-Xaa3-Xaa4-Xaa5-Ile-Ala-Trp-Xaa9-Xaa10-Xaa11-Xaa12-Xaa13-Xaa14-Xaa15 (2), the amino to carboxy direction being from left to right;
wherein:
each of Xaa1, Xaa2, and Xaa15 is independently absent or Ala, Arg, Lys or His;
Xaa3 is independently absent or Ala, Phe, Trp or Tyr;
each of Xaa4, Xaa5, and Xaa9 is independently absent or Phe, Trp or Tyr;
Xaa10 is independently absent or His, Lys or Arg;
Xaa11 is absent or Ala, Gly, Val, Leu, Ile, Pro, Cys or Met;
Xaa12 is absent or Ala; and
each of Xaa13 and Xaa14 is independently absent or Asn, Gln, Ser or Thr;
wherein the pharmacologically active peptide sequence of formula (2) has 5 or more contiguous amino acid residues.

In some embodiments, in formula (2), one or more amino acid residues of the group consisting of Xaa1, Xaa2, Xaa3, Xaa4, Xaa5, Xaa11, Xaa12, Xaa13, Xaa14, and Xaa15, are absent.

In some embodiments, the pharmacologically active peptide sequence of formula (2) is SEQ ID NO: 17, SEQ ID NO: 18, SEQ ID NO: 19, SEQ ID NO: 20, SEQ ID NO: 22, SEQ ID NO: 23, SEQ ID NO: 24 or SEQ NO ID: 5.

In some embodiments, the pharmacologically active peptide sequence of formula (2) has from 15 to 18 contiguous amino acid residues.

In some embodiments, the pharmacologically active peptide sequence of formula (2) has 18 contiguous amino acid residues.

In some embodiments, the peptide comprises at least a second peptide or protein.

In some embodiments, the invention relates to a composition comprising a peptide having a pharmacologically active peptide sequence of formula (1):

—Z—X—Z'—                     (1)

in which:
each of Z and Z' is a peptide independently comprising a cell penetration-enhancing amino acid sequence or an activity-enhancing amino acid sequences having from 2 to 15 naturally-occurring amino acids, wherein H, acetyl chloride, and trifluoroacetyl is covalently bonded to the N-terminus of —Z—X—Z'—, and X is the peptide X having a pharmacologically active peptide sequence of formula (2):
Xaa1-Xaa2-Xaa3-Xaa4-Xaa5-Ile-Ala-Trp-Xaa9-Xaa10-Xaa11-Xaa12-Xaa13-Xaa14-Xaa15 (2), the amino to carboxy direction being from left to right;
wherein:
each of Xaa1, Xaa2, and Xaa15 is independently absent or an Ala, or is an amino acid with a basic side chain (Arg, Lys or His);
Xaa3 is independently absent, or an Ala or is an amino acid with an aromatic side chain (Phe, Trp or Tyr)
each of Xaa4, Xaa5, and Xaa9 is independently absent or amino acid with an aromatic side chain (Phe, Trp or Tyr);
Xaa10 is independently absent or is an amino acid with a basic side chain (His, Lys or Arg);
Xaa11 is absent or is a non-polar amino acid (Ala, Gly, Val, Leu, Ile, Pro, Cys or Met);
Xaa12 is absent or Ala;
each of Xaa13 and Xaa14 is independently absent or, is an amino acid with an uncharged side chain (Asn, Gln, Ser or Thr);
wherein X has 5 or more amino acid contiguous residues.

In some embodiments, X has the following sequence: Ac-Arg-Ala-Tyr-Phe-Trp-Ile-Ala-Trp-Tyr-Lys-Leu-Ala-Asn-Ser-Lys-NH$_2$ (SEQ ID NO: 1).

In some embodiments, the peptide comprises a peptide of formula (1)

Z—X—Z'—                     (1)

in which:
X is the pharmacologically active peptide sequence of formula (2) as defined above; and
each of Z and Z' is a peptide independently comprising a cell penetration-enhancing amino acid sequence or an activity-enhancing amino acid sequence having from 2 to 15 naturally-occurring amino acids.

In some embodiments, H, acetyl, chloride, or trifluoroacetyl is covalently bonded to the N-terminus of —Z—X—Z'—.

In some embodiments, OH or NH$_2$ is covalently bonded to the C-terminus of —Z—X—Z—.

In some embodiments, Z is a peptide comprising a sequence including, from N- to C-terminus, amino acid residues Gly, Glu, and Arg, respectively, has a pharmacologically active peptide sequence of SEQ ID NO: 5, and Z' is absent.

In some embodiments, any peptide above is linked to a half-life enhancing moiety selected from albumin-binding moieties. In some embodiments, the peptide is one in which the peptide has a N-terminus which is acetyl, and a C-terminus which is NH$_2$.

In some embodiments, the peptide, in the form of a multimer, comprises two or more peptides having a sequence of formula (2) interspaced by amino acid-based cleavable linkers, e.g., by esterification of the C-terminal domain, wherein the multimer is optionally N-terminally acylated and the C-terminally amidated.

In some embodiments, the invention comprises pharmaceutical compositions containing the smooth muscle tone modulating peptides and pharmaceutically acceptable vehicles, excipients or additives, useful for the treatment of diseases associated to the deregulation of contractility of the smooth muscles. For example, in some embodiments, a pharmaceutical composition, comprises one or more peptides defined above and a pharmaceutically acceptable excipient.

III—Peptide Synthesis

The peptides of the present invention can be prepared by any methodologies known by those skilled in the art, including recombinant and non-recombinant methods. Synthetic pathways (non-recombinant) include, without limitation, solid phase chemical synthesis of the peptides, liquid phase chemical synthesis of the peptides, and biocatalyzed synthesis. In a preferred embodiment, the peptides are obtained by chemical synthesis, in liquid or solid phase, using manual, automated or semi-automated systems.

Solid phase peptide synthesis (SPPS), for example, is known and widely employed since the description by MERRIFIELD (MERRIFIELD, R. B. Solid Phase Peptide Synthesis. I. The Synthesis of a Tetrapeptide J. *Am. Chem. Soc.*, 85:2149-2154. 1963). A range of variations of SPPS is available to those skilled in the art (see GUTTE, B. Peptide Synthesis, Structures, and Applications. Academic Press, San Diego, Calif., Chapter 3, 1995; and WHITE, P. D., and CHAN, W. C. Fmoc Solid Phase Peptide Synthesis: A practical Approach. Oxford University Press, Oxford, 2004; MACHADO, A., LIRIA, C. W., PROTI, P. B., REMUZGO, C., MIRANDA, T. M. Sinteses química e enzimática de peptideos: princípios básicos e aplicações. *Quim. Nova*, 5:781-789 2004). Briefly, the construction of the peptide by SPPS occurs in the sense C→N terminus. For that purpose, the C-terminal amino acid of interest is coupled to a solid support. The amino acid to be attached subsequently has the N-terminal portion protected with a group Boc, Fmoc or another adequate protective radical while the C-terminal portion is activated with a standard coupling reagent. Subsequently, the free terminal amine of the amino acid bound to the support reacts with the terminal carboxy portion of the subsequent amino acid. The terminal amine of the dipeptide is then deprotected and the process is repeated until the polypeptide is complete. Whenever adequate, the starting amino acids can also have protections in the side chains.

Alternatively, the peptides of the present invention may be obtained by a recombinant method. Without limiting possible methodological variations, an exemplificative protocol includes: construction of the nucleic acid that encodes the peptide of interest; cloning of the said nucleic acid in an expression vector; transformation of a host cell (cells, vegetable, bacteria, such as *Escherichia coli*, yeasts, such as *Saccharomyces cerevisiae*, or mammal cells, such as Chines Hamster Ovary Cells) with the said vector; expression of the nucleic acid to produce the peptide of interest. Methods for production and expression of recombinant polypeptides in vitro and in prokaryotic and eukaryotic host cells are known to those skilled in the art (see U.S. Pat. No. 4,868,122, and SAMBROOK, J., FRITSCH, E. F., MANIATIS, T. Molecular Cloning: A Laboratory Manual. Ed. 2. Cold Spring Harbor Laboratory Press, 1989).

III.A—Correlated Peptides

Those that are skilled in the art acknowledge that certain modifications may be made on peptides such as those described in the present invention, causing small or no alterations to the properties of the said peptides. Therefore, peptides related to those demonstrated herein include analogues and/or derivatives that retain some or all of the therapeutic activity of the original peptides. In this context, the term "analogue" indicates variants obtained by substitutions, deletions or additions of amino acids to the peptides described herein; while "derivative" indicates variants containing chemical modifications on the primary sequence of the peptides described herein and/or their analogues. In certain aspects, such variants may evidence improvements in at least one of the therapeutic activities of the peptides. Additionally, the peptides of the present invention may be comprised of L-amino acids, D-amino acids or a combination of both in any ratio.

Another embodiment includes prodrugs or drug precursors that are chemically or enzymatically converted into any of the active peptides before, after or during the administration to a patient in need thereof. Such compounds may include among others esters, N-alkyl, phosphates or conjugates of amino acids (ARNAB, D E, Application of Peptide-Based Prodrug Chemistry in Drug Development; Springer, New York Heidelberg Dordrecht London, 2013), more lipophilic peptides (CACCETTA, R., BLANCHFIELD, J. T., HARRISON, J., TOTH, I., BENSON, H. A. E. Epidermal Penetration of a Therapeutic Peptide by Lipid Conjugation; Stereo-Selective Peptide Availability of a Topical Diastereomeric Lipopeptide. *International Journal of Peptide Research and Therapeutics*, 12 (3), 327-333. 2006), and in some cases, such compounds are made more hydrophilic by adding polar linkers, for example by esterification of the C-terminal domain.

The invention also includes any cyclic peptide able to be converted into any linear active peptide. It further includes chemical modification with bioconjugates or macromolecules such as e. glycosylation or pegylation (HUTTUNEN, K. M., RAUNIO, H., RAUTIO, J. Prodrugs—from Serendipity to Rational Design. *Pharmacol Rev.* 63:750-771, 2011).

The present invention further includes a peptidomimetic approach using any of the active peptides as a support to project active structures based on bioesters of groups of amino acids (VAGNER, J., QU, H. and HRUBY, V. J. Peptidomimetics, a synthetic tool of drug Discovery; *Curr Opin Chem Biol.* 12(3): 292-296. 2008.).

The present invention includes analogues containing 1, 2, 3, 4, 5, 6, 7, 8, 9, 10, 11 or 12 conservative or non-conservative amino acid substitutions related to the peptides here described. Desirable amino acid substitutions, either conservative or non-conservative, can be determined by those skilled in the art using routine methodologies. In a certain aspect of the invention, the smooth muscle tone modulating peptides include analogues containing conservative substitutions, which produce variants with functional and chemical characteristics similar to those of the original peptides. In another aspect, the analogues contain non-conservative substitutions, which can produce characteristics significantly distinct from those evidenced by the original peptides.

Natural amino acids may be classified in terms of the side chains properties of the as: nonpolar (nonpolar: (glycine (Gly), alanine (Ala), valine (Val), leucine (Leu), isoleucine (Ile), methionine (Met)); uncharged polar: (cysteine (Cys), serine (Ser), threonine (Thr), proline (Pro), asparagine (Asn), glutamine (Gln)); acid (aspartic acid (Asp), glutamic acid (Glu); basic (histidine (His), lysine (Lys), arginine (Arg)); and aromatic (tryptophan (Trp), tyrosine (Tyr), phenylalanine (Phe)). As an example, non-conservative substitutions may involve the exchange of an amino acid of a class for another from a different group; they may further be introduced into regions of the peptide that are not critical for the therapeutic activity. However, the substitutions are preferably conservative. That is, they involve the exchange of amino acid for another one of the same class. This type of modification also encompasses substitutions by artificial and/or nonessential amino acid residues, including peptidomimetics and other atypical forms of amino acids that can be regularly used during the synthesis of the peptide.

Strategies for defining substitutions of amino acids can be guided by the hydropathicity index of the side chains. The importance of hydropathic amino acids on the function of a polypeptide is understood by a person skilled in the art (KYTE, J. and DOOLITTLE. R. F. A simple method for displaying the hydropathic character of a protein. *J. Mol. Biol.* 157:105-31. 1982). Each amino acid has a hydropathicity index determined based on characteristics of hydrophobicity and charge. These are Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). Those skilled in the art understand that amino acids with similar hydropathicity indexes can be interchanged without significant loss of biological activity.

It is known that conservative substitutions can also be based on hydrophilicity. The average hydrophilicity of a polypeptide, determined by the hydrophilicity of the adjacent amino acids, is correlated with the biological properties of the compound. According to the U.S. Pat. No. 4,554,101, the natural amino acids have the following hydrophilicity values: Arg (+3.0); Lys (+3.0); Asp (+3.0±1); Glu (+3.0±1); Ser (+0.3); Asp (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

The conservative substitutions referred to in the present invention include, without limitations:

(SEQ ID NO: 2)
Ac-Arg-Gln-Tyr-Phe-Trp-Ile-Ala-Trp-Tyr-Lys-Leu-Ala-Asn-Ser-Ala-NH$_2$ (SEQ ID NO: 3)
Ac-Arg-Gln-Ala-Phe-Trp-Ile-Ala-Trp-Tyr-Lys-Leu-Ala-Asn-Ser-Lys-NH$_2$

```
                                                 (SEQ ID NO: 4)
Ac-Ala-Gln-Tyr-Phe-Trp-Ile-Ala-Trp-Tyr-Lys-Leu-
Ala-Asn-Ser-Lys-NH₂

(SEQ ID NO: 5)
Ac-Arg-Gln-Tyr-Phe-Trp-Ile-Ala-Trp-Tyr-Lys-Leu-
Ala-Asn-Ser-Lys-NH₂

(SEQ ID NO: 6)
Ac-Arg-Gln-Tyr-Phe-Trp-Ile-Ala-Trp-Tyr-Lys-Ile-
Ala-Ser-Asn-Lys-NH₂
```

In certain aspects of the invention, the analogues of the peptides include 1, 2, 3, 4, 5, 6, 7, 8, 9 or 10 amino acid deletions compared to the originally described peptides. The deleted amino acid(s) may be found in the N-terminal or C-terminal regions, on both flanks, internally to the sequence of the peptide or yet on one or both flanks and internally to the sequence. When the analogues have more than one deletion, the removed amino acids may be contiguous or may be located in different regions.

The deletions contemplated by the present invention include, without limitations:

```
                                                 (SEQ ID NO: 17)
Ac-Gln-Tyr-Phe-Trp-Ile-Ala-Trp-Tyr-Lys-Leu-Ala-
Asn-Ser-NH₂

(SEQ ID NO: 18)
Ac-Tyr-Phe-Trp-Ile-Ala-Trp-Tyr-Lys-Leu-Ala-Asn-NH₂

(SEQ ID NO: 19)
Ac-Phe-Trp-Ile-Ala-Trp-Tyr-Lys-Leu-Ala-NH₂

(SEQ ID NO: 20)
Ac-Arg-Gln-Tyr-Phe-Trp-Ile-Ala-Trp-Tyr-NH₂

(SEQ ID NO: 22)
Ac-Arg-Gln-Tyr-Phe-Trp-Ile-Ala-Trp-NH₂

(SEQ ID NO: 23)
Ac-Trp-Ile-Ala-Trp-Tyr-Lys-Leu-NH₂

(SEQ ID NO: 24)
Ac-Ile-Ala-Trp-Tyr-Lys-NH₂
```

Another aspect of the invention comprises analogues having 1, 2, 3, 4 or 5 additions of amino acids compared to the peptides originally described herein. The insertions in question may occur in the N-terminal or C-terminal regions, on both flanks, internally to the sequence of the peptide, or yet, on one or both flanks and internally to the sequence. When the analogues have more than one addition, the amino acids may be inserted contiguously or in distinct regions of the molecule.

The invention also comprises any combination of two or more of the active peptides, which are linked by a linking group and are converted in the sole active peptides or show the pharmaceutical activity as an entire molecule (HUTTUNEN, K. AND RAUTIO, J. Prodrugs—An Efficient Way to Breach Delivery and Targeting Barriers. *Current Topics in Medicinal Chemistry.* 11, 2265-2287. 2011). Insertions of amino acids also comprise linkers of amino acids, fusion peptides and permeation-enhancing sequences that may be added to the N-terminal or C-terminal regions of the peptides described herein. Peptides sequences able to enhance the cellular permeation and/or transcutaneous absorption are known by those skilled in the art and may be found, for example, in Kumar et al (KUMAR, S., NARISHETTY, S. T., TUMMALA, H. Peptides as Skin Penetration Enhancers for Low Molecular Weight Drugs and Macromolecules. In: Dragicevic N., Maibach H. (eds) Percutaneous Penetration Enhancers Chemical Methods in Penetration Enhancement. Springer, Berlin, Heidelberg. 2015) and in the U.S. Pat. No. 14,911,019 and WO2012064429.

In certain aspects, the above-mentioned linkers of amino acids, fusion peptides, and the permeation-enhancing sequences may have 2, 3, 4, 5, 6, 7, 8, 9, 10 or 15 additional amino acids, and can be connected to the smooth muscle tone modulating peptide by means of linking moieties as exemplified in SEQ ID NO: 28, SEQ ID NO: 29, and SEQ ID NO: 30. Such moieties may be an atom or a collection of atoms optionally used to link a therapeutic peptide to another therapeutic peptide. Alternatively, the connector molecule may consist of a sequence of amino acids designed for proteolytic cleavage in order to allow the release of the biologically active portion in an appropriate environment. Additionally, the smooth muscle tone modulating peptides described here may be fused to peptides designed to improve pharmacological properties (pharmacokinetic and/or pharmacodynamic) and or physicochemical properties.

The additions contemplated by the present invention include, without limitations:

```
                                                 (SEQ ID NO: 27)
Ac-Gly-Glu-Arg-Arg-Gln-Tyr-Phe-Trp-Ile-Ala-Trp-
Tyr-Lys-Leu-Ala-Asn-Ser-Lys-NH₂

(SEQ ID NO: 28)
Ac-Ile-Ala-Trp-Tyr-Lys-Gly-Gly-Gly-Gly-Gly-Ile-
Ala-Trp-Tyr-Lys-NH₂

(SEQ ID NO: 29)
Ac-Ile-Ala-Trp-Tyr-Lys-Arg-Gly-Gly-Gly-Gly-
Arg-Lys-Tyr-Trp-Ala-Ile-NH₂

(SEQ ID NO: 30)
Ac-Ile-Ala-Trp-Tyr-Lys-Gly-Gly-Gly-Gly-Gly-Ile-
Ala-Trp-Tyr-Lys-Gly-Gly-Gly-Gly-Gly-Ile-Ala-Trp-
Tyr-Lys-NH₂
```

In some aspects, the invention includes derivatives containing chemical modifications with one or more methyl or another small alkyl group in one or more positions of the peptide chain. Examples of such groups include methyl, ethyl, propyl, isopropyl, butyl, isobutyl, pentyl, etc. Alternatively, the derivatives result from the attachment of one or more glycosidic moieties to the peptide sequence. For example, the cited derivatives may be obtained by the attachment of one or more monosaccharides, disaccharides or trisaccharides to the peptide sequence. For example, the said derivatives may be obtained by the attachment of one or more monosaccharides, disaccharides or trisaccharides, at any position of the peptide. The glycosylation may be directed to native amino acids of the peptide, or alternatively, one amino acid can be substituted or added to receive the modification.

The said glycosylated peptides may be obtained by way of routine SPPS techniques, in which the glyco-amino acids of interest are prepared prior to the synthesis of the peptide and subsequently added to the sequence in the desired position. Therefore, smooth muscle tone modulating peptides may be glycosylated in vitro. In this case, the glycosylation may occur previously. Documents U.S. Pat. No. 5,767,254, WO 2005/097158, and DOORES et al (DOORES, K., GAMBLIN, D. P. AND DAVIS, B. G. Exploring and exploiting the therapeutic potential of glycoconjugates. *Chem. Commun.,* 1401-1403, 2006), incorporated herein for the sake of reference, describes the glycosylation of amino acids. As an example, the alpha or beta selective glycosylation of residues of serine and threonine may be achieved using the Koenigs-Knorr reaction and the methodology of anomerization in situ of Lemieux using intermediary Schiff bases. The deprotection of the glycosylated Schiff base is then conducted in slightly acid conditions or by means of hydrogenolysis.

Among the monosaccharides that can be introduced into one or more residues of amino acids of the peptides described herein are glucose (dextrose), fructose, galactose, and ribose. Other monosaccharides potentially adequate for use are glyceraldehydes, dihydroxyacetone, erythrose, threose, erythrulose, arabinose, lyxose, xylose, ribulose, xylulose, allose, altrose, mannose, N-acetylneuraminic acid, fucose, N-acetylgalactosamine, N-acetylglucosamine, among others. Glycosides, such as mono-, di- and trisaccharides for use in the modification of the smooth muscle tone modulating peptides may be of synthetic or natural origin. Disaccharides that can be introduced into one or more residues of the amino acids described herein include sucrose, lactose, trehalose, alose, melibiose, cellobiose, and others. The trisaccharides can be acarbose, raffinose, and melezitose.

In additional aspects of the invention, the smooth muscle tone modulating peptides may be coupled to biotin. Such peptide-biotin complexes may then be coupled to avidin.

As previously mentioned, the peptides described herein can be modified to exhibit only a partial reduction or no reduction of the biological activities and properties of the said peptides. In some cases, such modifications can be realized to result in an improvement of the intended therapeutic activity. Therefore, the scope of the present invention includes variants that retain at least 1%, 5%, 10%, 20%, 30%, 40%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99%, and any range derivable therefrom such that, for example, at least 70% to at least 80%, and preferably at least 81% until 90%, or yet more preferably, between 91% and 99% of the therapeutic activity relatively to the non-modified peptide. The scope of the present invention also includes variants that have therapeutic activity higher than 100%, 110%, 125%, 150%, 200% or more than 300%, or yet that evidence a 100 or 100 times higher activity, and any range derivable therefrom, in comparison with the non-modified peptides.

The smooth muscle tone modulating peptides described in the present invention may also be covalently conjugated to hydrosoluble polymers, either directly or by means of a spacer group. Examples of peptide-polymer conjugates inserted in the scope of this invention include: conjugates containing a hydrosoluble polymer coupled to the peptide in a detachable or stable manner, particularly coupled to the N-terminal portion; conjugates containing a hydrosoluble polymer coupled to the peptide in a detachable or stable manner, particularly coupled to the C-terminal portion; conjugates containing a hydrosoluble polymer coupled to the peptide in a detachable or a stable manner, particularly coupled to an amino acid located internally in the peptidic chain; conjugates containing more than one hydrosoluble polymer coupled to the peptide in a detachable or a stable manner, coupled to the peptide in distinct regions such as, for example, to the N-terminal portion and to the side chain of an amino acid located internally in the peptidic sequence (particularly a lysine). Alternatively, an amino acid, to which the hydrosoluble will be coupled, may be inserted in the N-terminal or C-terminal portions, or in the middle of the primary structure of the peptide.

Typically, the above-contemplated polymer is hydrophilic, non-peptidic, biocompatible and non-immunogenic. In this respect, a substance is deemed biocompatible if the beneficial effects associated with the administration thereof to living organisms, either alone or combined with another substance (for example, a biologically active ingredient such as a therapeutic peptide), overcomes any deleterious effect that is clinically observable. A substance is deemed non-immunogenic if the intended use of the substance in vivo does not produce an undesirable immunological response (for example, the formation of antibodies) or, if an immunological response is triggered, such event is not deemed clinically significant or important. Example of such hydrosoluble polymers include, without limitation: polyethylene glycol (PEG), polypropylene glycol (PPG), copolymers of ethylene glycol and propylene glycol, polyolefinic alcohol, polyvinylpyrrolidone, poly(hydroxyalkyl methacrylamide), poly(hydroxyalkyl methacrylate), sulfated of non-sulfated polysaccharides, polyoxazolines, poly(N-acryloylmorpholine), and combinations of these polymers, including copolymers and terpolymers thereof.

The above-cited hydrosoluble polymers are not limited to a particular architecture and may have linear of no-linear structures, such as branched, bifurcated, multi-branched (for example, PEGs coupled to a polyol core), or dendritic (densely branched structure with several terminal groups). Methods for the conjugation of polymers to peptides are described in the prior art, as well as the adequate reagents, which may be selected among alkylating or acylating agents (see HARRIS, J. M. and ZALIPSKY, S., Poly(ethylene glycol), Chemistry and Biological Applications. ACS, Washington, 1997; VERONESE, F., and HARRIS, J. M. Peptide and Protein PEGylation. *Advanced Drug Delivery Reviews,* 54(4); 453-609. 2002; ZALIPSKY, S., LEE, C. Use of Functionalized Poly(Ethylene Glycols) for Modification of Polypeptides. in Polyethylene Glycol Chemistry: Biotechnical and Biomedical Applications, J. M. Harris, ed., Plenus Press, New York, 1992; ZALIPSKY, S. Functionalized poly(ethylene glycol) for preparation of biologically relevant conjugates. *Advanced Drug Reviews,* 16:157-182, 1995; and in ROBERTS, M. J., BENTLEY, M. D., HARRIS, J. M., Chemistry for peptide and protein PEGylation. *Adv. Drug Delivery Reviews,* 54, 459-476, 2002). Typically, the average molecular weight of hydrosoluble polymers may vary between 100 Daltons (Da) and 150,000 Da (150 kDa). For example, there may be used hydrosoluble polymers with an average molecular weight of 250 Da to 80 kDa, from 500 Da to 65 kDa, from 750 Da to 40 kDa, or 1 kDa to 30 kDa. In an additional aspect of the invention, the smooth muscle tone modulating peptides may be acylated in one or more positions of the peptide chain in order to improve physicochemical, pharmacokinetic and/or pharmacodynamic characteristics. For example, the introduction of lipophilic acyl groups is widely employed to increase the plasma half-life of therapeutic peptides, since they render the groups coupled thereto less susceptible to oxidations. Methods and reagents for acylation of peptides are known to those familiar with the art. Documents WO 98/08871, US 2003/0082671, WO 2015/162195, incorporated herein as references, exemplify reagents and conditions for acylation of peptides. The modification of free amines with acyl groups is particularly useful to promote the acylation of peptides and proteins (ABELLO, N., KERSTJENS, H. A., POSTMA, D. S., BISCHOFF, R. Selective acylation of primary amines in peptides and proteins. *Journal of proteome research,* 6(12): 4770-4776. 2007). In this particular case, the smooth muscle tone modulating peptides may be acylated at the N-terminal amine or in the side chain of one or more amino acids originally present in the sequence or inserted for the purpose of receiving the acylation in question.

IV—Pharmaceutical Forms

In one aspect of the present invention, there are provided pharmaceutical forms comprising one or more peptides of the present invention. In a particular modality, the peptides of the present invention are combined with a pharmaceutically acceptable vehicle and/or excipient and/or additive.

The pharmaceutical forms of the invention can be prepared and formulated in accordance with the conventional methods such as disclosed, for example, in the British, European and United States Pharmacopeias (British pharmacopoeia. Vol. 1. London: Medicines and Healthcare products Regulatory Agency; 2018; European pharmacopoeia. 9th ed, Strassbourg: Council of Europe: 2018; United States Pharmacopoeia, 42, National Formulary 37, 2018), Remington's Pharmaceutical Sciences (REMINGTON, J. P., AND GENNARO, A. R. Remington's Pharmaceutical Sciences. Mack Publishing Co., 18th ed. 1990), Martindale: The Extra Pharmacopoeia (MARTINDALE, W. AND REYNOLDS, J. E. F. Martindale: The Extra Pharmacopoeia. London, The Pharmaceutical Press $31^{st}$ ed, 1996) and Harry's Cosmeticology (HARRY, R. AND ROSEN, M. R. Harry's cosmeticology. Leonard Hill Books, $9^{th}$ ed. 2015), Pharmaceutical technology (PRISTA, L. V. N., ALVES, A. C., MORGADO, R. M. R. Técnica Farmacêutica e Farmácia Galênica. $4^{th}$ ed. Fundação Calouste Gulbenkian. Serviçco de Educação e Bolsas, 1996).

The pharmaceutical forms may comprise, for example, one or more parts of water, buffers (for example, sodium bicarbonate, buffered neutral saline solution of saline solution buffered with phosphate), ethanol, mineral oil, vegetable oil, dimethyl sulfoxide, carbohydrates (for example, lactose, sorbitol, trehalose, glucose, mannose, sucrose, amide, glycerol, mannitol or dextrans), proteins, adjuvants (such as stabilizers like polymers and cyclodextrins), polypeptides or amino acids (such as His, Gly, Lys, Asp, Glu and Arg), antioxidants (such as ascorbic acid, alpha-tocopherol, sulfites, BHA (butylhydroxyanisole), BHT (butylhydroxytoluene), surfactant agents (such as non-ionic detergents—Triton X-100, polysorbate 20, polysorbate 80, Pluronic F68, Pluronic F88, Pluronic F127, Brij 35), chelating agents (such as EDTA and/or glutathione) and/or preservatives (such as parabens, sorbic acid, imidazole urea, ammonia quaternarium compounds hydantoin, phenolic derivatives, acidic derivatives halogenated compounds).

Pharmaceutical forms can be formulated for any route of administration including, for example, topical, oral nasal, rectal or parenteral administration. The term parenteral, as used herein, includes subcutaneous injection, intradermic injection, intravascular injection (for example, intravenous), intramuscular injection, spinal injection, intracranial injection, intrathecal injection, and intraperitoneal injection, as well as any similar technique of injection or infusion. In certain modalities, compositions for oral use are preferred. Such compositions include, for example, pills, tablets, solutions, aqueous or oily suspensions, dispersible powders or granules, emulsions, hard or soft capsules or syrups or elixirs. Among other modalities, pharmaceutical compositions may be formulated with a freeze-dried powder.

Pharmaceutical forms intended for oral use may further comprise other components, such as sweetening agents, flavoring agents, coloring agents and/or preservative agents in order to provide attractive and palatable preparations.

Pills have the active ingredient mixed with physiologically compatible excipients that are adequate for the manufacture of pills. Such excipients include, for example, inert diluents (for example, calcium carbonate, sodium carbonate, lactose, calcium phosphate or sodium phosphate), granulation and disintegration agents (for example, corn starch or alginic acid), bonding agents (for example, starch, gelatin or acacia), and lubricating agents (for example, magnesium stearate, stearic acid or talcum). Pills may be formed using standard techniques, including dry granulation, direct compression, and wet granulation. The pills may not be coated, or they may be coated using known techniques.

Formulations for oral use may also be presented as hard gelatinous capsules wherein the active ingredient is mixed with an inert solid diluent (for example, calcium carbonate, calcium phosphate, kaolin, talcum, monohydrated lactose, colloidal silicon dioxide, microcrystalline cellulose, sodium lauryl sulfate, sodium amide glycolate) or as soft gelatinous capsules, wherein the active ingredient is mixed with water or an oily medium (for example, peanut oil, liquid vaseline or olive).

Aqueous suspensions contain the active material(s) mixed with adequate excipients, such as suspension agents (for example, sodium cellulose carboxymethyl, methylcellulose, hydroxypropyl methylcellulose, sodium alginate, polyvinylpyrrolidone, tragacanth gum, and acacia gum); and dispersion or wetting agents (for example, naturally occurring phosphatides, such as lecithin, products of condensation of an alkylene oxide with fatty acids, such as polyoxyethylene stearate, products of condensation of ethylene oxide with long-chain aliphatic alcohols, such as heptadeca-ethyleneoxy-cetanol, products of the condensation of ethylene oxide with partial esters derived from fatty acids and one hexitol, such as sorbitol polyoxyethylene mono-oleate or products of the condensation of ethylene oxide with partial esters derived from fatty acids and hexitol anhydrides, such as mono-oleate of polyethylene sorbitan). Aqueous suspensions may also comprise one or more preservatives, such as ethyl p-hydroxybenzoate or n-propyl, one or more coloring agents, one or more flavoring agents and/or one or more sweetening agents, such as sucrose or saccharine.

Oily suspensions can be formulated by means of the suspension of the active ingredient(s) in vegetable oil (for example, peanut oil, olive oil, sesame oil or coconut oil) or in mineral oil, such as liquid paraffin. The oily suspensions may contain a thickening agent, such as bee wax, hard paraffin or cetyl alcohol. Sweetening agents, such as those presented above and/or flavoring agents may be added to provide palatable oral preparations. Such suspensions may be preserved by means of the addition of an antioxidant, such as ascorbic acid.

Dispersible powders and granules adequate for the preparation of an aqueous suspension by means of the addition of water provide the active ingredient in a mixture with a dispersion agent or wetting agent, a dispersion agent and one or more preservatives. Adequate dispersion agents or wetting agents are exemplified by those already mentioned above. Additional excipients, such as sweetening agents, flavoring agents, and coloring agents may also be present.

Pharmaceutical forms may also be formulated as water-in-oil emulsions. The oily phase may be a vegetable oil (for example, coconut oil, almonds oil, grape seed oil, olive oil or peanut oil), a mineral oil (for example, liquid Vaseline), or a mixture thereof. Adequate emulsifying agents include naturally occurring gums (for example, acacia gum or tragacanth gum), naturally occurring phospholipids (for example, phosphatidylserine), anhydrides (for example, monooleate of sorbitan) and products of condensation of partial esters derived from fatty acids and hexitol with ethylene oxide (for example, mono-oleate of polyoxyethylene sorbitan). An emulsion can also comprise one or more sweetening agents and/or flavorizers.

Syrups and elixirs may be formulated with sweetening agents, such as glycerol, propylene glycol, sorbitol or sucrose. Such formulations may also comprise one or more preservatives, flavoring agents and/or coloring agents.

Formulations for topical administration typically comprise a topical vehicle combined with the active agent(s), with or without additional optional components. Adequate additional components and topical vehicles are well known in the art and it will be obvious that the choice of a vehicle will depend on the physical form and mode of administration in particular. Topical vehicles include water; organic solvents, such as alcohols (for example, ethanol or isopropyl alcohol) or glycerin; glycols (for example, butylene, isoprene or propylene glycol); aliphatic alcohols (for example, lanoline); mixtures of water and organic solvents and mixtures of organic solvents, such as glycerin alcohol; lipid-based materials, such as fatty acids, acylglycerols (including oils, such as mineral oil and animal or synthetic fats), phosphoglycerides, sphingolipids and waxes; protein-based materials, such as collagen and gelatin; silicone-based materials (volatile and nonvolatile); and hydrocarbon-based materials, such as microsponges and polymeric matrixes. A composition may further include one or more components adapted to improve the stability or efficacy of the formulation that is applied, such as stabilizing agents, suspension agents, emulsifying agents, viscosity adjusters, gelling agents, preservatives, antioxidants, skin penetration enhancers, humectants, and sustained release materials. Examples of such components are described in Martindale: The Extra Pharmacopoeia (MARTINDALE, W. AND REYNOLDS, J. E. F. Martindale: The Extra Pharmacopoeia. $31^{st}$ ed, London, The Pharmaceutical Press. 1996) and Remington: The Science and Practice of Pharmacy, (Remington: The Science and Practice of Pharmacy, Lippincott Williams & Wilkins, Philadelphia, Pa., $21^{st}$ ed., 2005). Formulations may comprise microcapsules, such as microcapsules of hydroxymethyl cellulose or gelatin, liposomes, microspheres of albumin, microemulsions, nanoparticles or nanocapsules.

A topical formulation can be prepared through any one a variety of physical forms including, for example, solids, pastes, creams, foams, lotions, gels, powders, aqueous liquids, and emulsions. The physical appearance and viscosity of such pharmaceutically acceptable forms can be oriented by the presence and quantity of emulsifier(s) and viscosity adjuster(s) present in the formulation.

Solids are in general firm and non-pourable and are commonly formulated as bars or clubs or in the form of particles; solids may be opaque or transparent and may optionally contain solvents, emulsifiers, humectants, emollients, fragrances, colorants/dyes, preservatives and other active ingredients that enhance or intensify the effectiveness of the final product.

Creams and lotions are frequently similar to one another, differing mainly in terms of their viscosity; lotions and creams may be opaque, translucid or transparent, and frequently contain emulsifiers, solvents, and agents for adjustment of viscosity, as well as humectants, emollients, fragrances, colorants/dyes, preservatives and other active ingredients that enhance or increase the effectiveness of the final product.

Gels may be prepared with a series of viscosities, from thick with high viscosity to thin with low viscosity. Those formulations, as well as those of lotions and creams, can also contain solvents, emulsifiers, humectants, emollients, fragrances, colorants/dyes, preservatives and other active ingredients that enhance or increase the effectiveness of the final product.

Liquids are thinner than creams, lotions or gels and frequently do not contain emulsifiers. Liquid topical products frequently contain solvents, emulsifiers, humectants, emollients, fragrances, colorants/dyes, preservatives and other active ingredients that enhance or increase the effectiveness of the final product.

Emulsifiers adequate for use in topical formulations include, without limitations, ionic emulsifiers, ceteralylic alcohol, non-ionic emulsifiers, such as polyoxyethylene oleyl ether, PEG-40 stearate, cetearyl alcohol such as ceteareth-12, ceteareth-20, ceteareth-30, PEG-100 stearate, and glyceryl stearate. Adequate agents for the adjustment of viscosity include, without limitation, protective colloids of non-ionic gums, such as hydroxyethyl cellulose, xanthan gum, aluminum magnesium silicate, silica, microcrystalline wax, bee wax, paraffin, and cetyl palmitate. A gel composition may be formed by means of the addition of a gelling agent, such as chitosan, methylcellulose, ethyl cellulose, polyvinyl alcohol, polyquaterniums, hydroxyethyl cellulose, hydroxypropyl cellulose, hydroxypropyl methylcellulose, carbomer or glycyrrhizinate with ammonia. Adequate surfactants include, without limitations, non-ionic surfactants, amphoteric surfactants, ionic surfactants, and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, chloride of cocamidopropyl phosphatidyl PG-diammonium and ammonium laureth sulfate can be used in topical formulations. Adequate preservatives include, without limitations, antimicrobials, such as methylparaben, propylparaben, sorbic acid, benzoic acid, and formaldehyde, as well as physical stabilizers and antioxidants, such as vitamin-E, ascorbic acid, and propyl gallate. Adequate humectants include, without limitations, lactic acid and other hydroxy acids and their salts, glycerin, propylene glycol, and butylene glycol. Adequate emollients include derivatives of lanolin, petrolatum, isostearyl neopentanoate, and mineral oils. Adequate fragrances and colorants include, without limitations, FD&C Red No. 40 and FD&C Yellow No. 5. Other adequate additional ingredients that may be used topically include, without limitations, abrasives, absorbents, anti-foaming agents, anti-static agents, astringents (for example, hamamelis, alcohol and herbal extracts, such as chamomile extract), binders/excipients, buffering agents, chelating agents, film-forming agents, conditioning agents, propellants, opacifying agents, pH regulators and protectors.

Among the formulations for topical use one may further point out cutaneous permeation promoter excipients which may function is to enhance the release of the compound on the surface of the skin, through the stratum corneum, in a transdermic system. The main promoters of permeation used in the release of pharmaceuticals include alcohols, glycols and glycerides, such as ethanol, propylene glycol, ethoxy diglycol, 1-decanol, 2-(2-ethoxyethoxy)ethanol; fatty acids and esters, such as palmitic acid, capric acid, oleic acid, myristic acid, or lauric acid (KANIKKANNAN, N. K., KANDIMALLA, K., LAMBA, S. S., SINGH, M. Structure-Activity Relationship of Chemical Penetration Enhancers in Transdermal Drug Delivery. *Current Medicinal Chemistry*, 7(6): 593-608. 2000; JAVADZADEH Y., ADIBKIA K., HAMISHEKAR H. Transcutol® (Diethylene Glycol Monoethyl Ether): A Potential Penetration Enhancer. In: Dragicevic N., Maibach H. (eds) *Percutaneous Penetration Enhancers Chemical Methods in Penetration Enhancement.* Springer, Berlin, Heidelberg, 2015.); sulfoxides, such as dimethylsulfoxide and dimethylformamide (WIECHERS, J. W. AND DE ZEEUW, R. A. Transdermal drug delivery: efficacy and potential applications of the penetration enhancer Azone. *Drug Des Deliv.* (2):87-100. 1990); phospholipids, such as phosphatidylglycerol, phosphatidylcholine and phosphatidylethanolamine; cyclodextrins (α-cyclodextrin, β-cyclodextrin and γ-cyclodextrin); dodecyl-N,N-dimethylamino acetate (DDAA); polymers such as already cited previously herein; small peptides such as, for example ACSSSPSKHCG, and digestive enzymes such as trypsin, papain, bromelain (MAGNUSSON, B. M. and RUNN, P. Effect of Penetration Enhancers on the Permeation of the Thyrotropin Releasing Hormone Analogue PGlu-3-Methyl-His-Pro Amide through Human Epidermis. *International Journal of Pharmaceutics,* 178(2):149-59. 1999; HOU, Y. W., CHAN, M. H., HSU, H. R., LIU, B. R., CHEN, C. P., CHEN, H. H., LEE, H. J. Transdermal Delivery of Proteins Mediated by Non-Covalently Associated Arginine-Rich Intracellular Delivery Peptides. *Experimental Dermatology,* 16(12): 999-1006. 2007; LANE, M. E. Skin penetration enhancers. *Int J Pharm.* 15; 447(1-2):12-21. 2013). Other pathways for permeation enhancers comprise physical methods such as iontophoresis (RAIMAN, J., KOLJONEN, M., HUIKKO, K., KOSTIANEN, R., HIRVONEN, J. Delivery and Stability of LHRH and Nafarelin in Human Skin: The Effect of Constant/Pulsed Iontophoresis. *European Journal of Pharmaceutical Sciences: Official Journal of the European Federation for Pharmaceutical Sciences,* 21(2-3): 371-77. 2004), electroporation (WANG, Y., TRAKUR, R., FAN, Q., MICHNIAK, B. Transdermal Iontophoresis: Combination Strategies to Improve Transdermal Iontophoretic Drug Delivery. *European Journal of Pharmaceutics and Biopharmaceutics: Official Journal of Arbeitsgemeinschaft Fur Pharmazeutische Verfahrenstechnik,* 60(2): 179-91. 2005), and, phonophoresis (PARK, E. J., WERNER, J., SMITH, N. B. Ultrasound Mediated Transdermal Insulin Delivery in Pigs Using a Lightweight Transducer. *Pharmaceutical Research,* 24(7): 1396-1401. 2007).

Typical modes of administration for topical compositions for external use include direct application of the product using the hands with the use of glove; or indirect application using a physical applicator, such as a spatula, a dosing syringe, a dosing rule, adhesive or stick; spraying (including mist spraying, aerosol or foam); use of single-dose sachets of 1 ml; application with a drop counter; dispersion and rinsing. One other form of indication for topical use is inhalation, or application in other different tissues of the skin, such as eyedrops applied in the conjunctive tissue or otological solutions for auricular application.

These inhalator formulations, in an exemplary form, include gaseous forms in aerosol (using a conventional propellant, for example, dichlorofluoromethane or trichlorofluoromethane), or particulates in the form of spray drying and emulsions, solutions or suspensions for liquids inhaled by nebulization. Further, we may exemplify a pharmaceutical form by ophthalmic or conjunctival pathway, cold creams, post-reconstituted, eye drops in isotonic suspensions or sterile suspensions dispensed by an eye dropper, and by otological pathway, cold creams or liquid isotonic pharmaceutical forms also dispensed with a drop dispenser.

In an exemplary mode, however, without limiting the possible formulations, the peptides of the present invention may be formulated in compositions of α-cyclodextrin, hydroxyethylcellulose, PEG6000, PEG400, hydroxypropyl β-cyclodextrin, emulsifier and stabilizer polysorbate 20 (tween 20) or 80 (tween 80).

A pharmaceutical form may be prepared as a sterile injectable aqueous or oily suspension. The compound(s) provided herein, depending on the vehicle and the concentration used, may be suspended or dissolved in such composition may be formulated in accordance with the known technique using adequate dispersion agents, wetting agents and/or suspension agents, such as those mentioned hereinabove. Among the acceptable vehicles and solvents that may be employed are water, 1,3-butanediol, Ringer's solution and isotonic solution of sodium chloride, sodium citrate and excipients that may include adjuvants such as complexes of inclusion with cyclodextrins, or releasing systems such as nanoemulsions, nanosuspensions, microemulsions, polymeric micelles, liposomes, niosomes, transfersomes and ethosomes (MELKAMU, G., WOHLRAB, J., NEUBERT, R. H. Dermal Delivery of Desmopressin Acetate Using Colloidal Carrier Systems. *The Journal of Pharmacy and Pharmacology,* 57(4):423-27. 2005; GOEBEL, A. S. B., SCHMAUS, G., NEUBERT, R. H., WOHLRAB, J. Dermal Peptide Delivery Using Enhancer Molecules and Colloidal Carrier Systems—Part I: Carnosine. *Skin Pharmacology and Physiology,* 25(6):281-87. 2012; MANOSROI, A., KHANRIN, P., LOHCHAROENKAL, W., WERNER, R. G., GOTZ, F., MANOSROI, W., MANOSROI, J. Transdermal Absorption Enhancement through Rat Skin of Gallidermin Loaded in Niosomes. *International Journal of Pharmaceutics,* 392(1-2): 304-10. 2010; EL MAGHRABY, G. M., WILLIAMS, A. C., BARRY, B. W. Skin Delivery of Oestradiol from Deformable and Traditional Liposomes: Mechanistic Studies. *The Journal of Pharmacy and Pharmacology,* 51(10):1123-34. 1999; DAYAN, N., and E. TOUITOU. Carriers for Skin Delivery of Trihexyphenidyl HCl: Ethosomes vs. Liposomes. *Biomaterials,* 21(18): 1879-85. 2000).

Furthermore, sterile fixed oils can be employed as a solvent or a suspension medium. For that purpose, any soft fixed oil can be used, including synthetic monoglycerides or synthetic diglycerides. Furthermore, fatty acids, such as oleic acid, are useful in the preparation of injectable compositions and adjuvants, such as local anesthetics, preservatives and/or buffering agents can be dissolved in the vehicle.

Pharmaceutical forms can also be formulated as suppositories (for example, for rectal administration). Such compositions can be prepared by mixing the drug with an adequate non-irritating excipient that is solid at ambient temperatures but becomes liquid at the rectal temperature and therefore will dissolve in the rectum to release the drug.

Pharmaceutical forms may be formulated to be released at a predetermined rate. An instant release may be obtained, for example, via sublingual administration (that is, administration through the mouth in such a manner that the active ingredient(s) is/are rapidly absorbed through the blood vessels of the sublingual plexus).

Formulations with a controlled release (that is, formulations such as a capsule, pill or coated table that diminishes and/or delays the release of the active ingredient(s) after administration) may be administered, for example orally, rectally or subcutaneously or through an implant in a target location. In general, a formulation with controlled release may be obtained by means of the combination of the active ingredient(s) with a matrix material that, in itself, changes the release rate and/or through the use of a coating with controlled release, which delays the disintegration and absorption in the intestinal tract (or location of implant), and thereby provides a delayed or a sustained action during a longer period. One such type of formulation with a controlled release is a formulation with sustained release, in which at least one active ingredient is continuously released during a period of time at a constant rate. Preferably, the therapeutic agent is released at a rate such that the concentrations in the blood (for example, plasma) are maintained within the therapeutic range, however below the toxic levels, during a period of time that is at least 4 hours, preferably at least 8 hours, and more preferably at least 12 hours. Such formulations may, in general, be prepared using well-known technologies. Vehicles for use inside such formulations are biocompatible, and may also be biodegradable. Preferably, a formulation provides a constant level of release of the modulator. The amount of modulator contained in a formulation with sustained release depends, for example, on the location of the implant, the expected release rate and duration and the nature of the condition to be treated or prevented.

The release rate may be varied using methods well known in the art including (a) variation of thickness of composition of the coating, (b) alteration of the quantity of manner of addition of plasticizer on a coating (c) inclusion of additional ingredients, such as agents that modify the release, (d) alteration of the composition, particle size or format of particle of the matrix and (e) provision of one or more passages through the coating. The amount of modulator contained within a sustained release formulation depends, for example, from the method of administration (for example, the location of the implant), the rate and duration of release that is expected and the nature of the condition to be treated or prevented.

The matrix material, which in itself may or not serve a controlled release function, is generally any material that support(s) the active ingredient(s). For example, a material such as a glyceryl monostearate or glyceryl diesterate may be employed. Active ingredient(s) may be combined with the matrix material prior to the formation of the dosage form (for example, a pill). Alternatively, or furthermore, the active ingredient(s) may be coated on the surface of a particle, granule, sphere, microsphere, globule or pellet that comprises the matrix material. Such coating may be obtained via conventional means, such as through dissolution of the active ingredient(s) in other or another adequate solvent and spraying. Optionally, extra ingredients are added prior to the coating (for example, to aid in the binding of the active ingredient(s) to the matrix material). The matrix may then be coated with a barrier agent before the application of the controlled release coating. Multiple coated matrix units may, if desired, be encapsulated to generate the final dosage form.

The controlled release coating may be a film, continuous and uniform, capable of supporting pigments and other additives, non-toxic, inert and devoid of adherence. Coatings that regulate the release of the modulator include pH-independent or dependent coatings, which can be used to release the modulator in the stomach and enteric coatings (which permit the formulation to pass intact through the stomach, and in the small intestine the coating dissolves and the contents are absorbed by the body). pH-dependent coatings include, for example, shellac, cellulose acetate phthalate, polyvinyl acetate phthalate, cellulose methyl hydroxypropyl phthalate, copolymers of an ester of methacrylic acid and zeine.

In certain modalities, the coating is a hydrophobic material, preferably used in an amount effective to reduce the hydration of the gelling agent after administration. Adequate hydrophobic materials include alkyl celluloses (for example, ethyl cellulose or carboxymethyl cellulose ethers), cellulose ethers, cellulose esters, acrylic polymers (for example, (poly)acrylic acid, (poly)methacrylic acid, copolymers of acrylic acid and methacrylic acid, copolymers of methyl methacrylate, ethoxy ethyl methacrylate, copolymer of alkamide/methacrylic acid, (poly)methyl methacrylate, polyacrylamide, ammonium methacrylate copolymer, aminoalkyl methacrylate copolymer, (poly)methacrylic acid anhydride and glycidyl methacrylate copolymers) and mixtures thereof.

Aqueous dispersions representative of ethyl cellulose includes, for example, AQUACOAT® (FMC Corp., Philadelphia, Pa.) and SURELEASE® (Colorcon, Inc., West Point, Pa.), both being applicable to the substrate according to the manufacturer's instructions. Representative acrylic polymers include, for example, the various polymers EUDRAGIT® (Rohm America, Piscataway, N.J.), which can be alone or in combination, depending on the desired release profile.

The physical properties of coatings that comprise an aqueous dispersion of hydrophobic material may be improved by means of the addition of one or more plasticizers. Plasticizers adequate for alkyl celluloses include, for example, dibutyl sebacate, diethyl phthalate, triethyl citrate, tributyl citrate, and triacetin. Plasticizers adequate for acrylic polymers include, for example, citric acid esters, such as triethyl citrate and tributyl citrate, dibutyl phthalate, polyethylene glycols, propylene glycol, diethyl phthalate, castor-oil plant, and triacetin.

Controlled release coatings are in general applied using conventional techniques, such as by means of spraying in the form of an aqueous dispersion. If so desired, the coating may comprise pores or channels to facilitate the release of the active ingredient. Pores and channels may be generated using well-known methods, including the addition of an organic or inorganic material that is dissolved, extracted or released from the coating in the environment of use. Some of such pore-formation materials include hydrophilic polymers, such as hydroxyalkyl celluloses (for example, hydroxypropyl methylcellulose), cellulose ethers, water-soluble synthetic polymers (for example, polyvinylpyrrolidone, cross-linked polyvinylpyrrolidone, and polyethylene oxide), water-soluble polydextrose, saccharides and polysaccharides, and alkaline metal salts.

The amount of active ingredient that can be combined with the materials of the vehicle to produce a unit dose will vary depending, for example, from the patient that is being treated, from the mode of administration in particular and any other co-administered drugs. Dosage units generally contain between about 5 pg to about 2 g of the active ingredient. Optimal dosages may be established using tests and routine procedures that are well known in the art.

In one aspect of the present invention, the compositions can comprise, in addition to the one or more smooth muscle tone modular peptides of the present invention, one or more additional active ingredients that include, without limitations, for example, analgesics, anti-inflammatory agents, anti-helminthic agents, anti-arrhythmia agents, antibiotics, anticoagulants, thrombolytic agents, diuretics, anti-depressives, anti-diabetic agents, anti-epileptic agents, anti-histaminic agents, anti-hypertensive agents, anti-muscarinic agents, anti-mycobacterial agents, anti-neoplastic agents, immunosuppressants, immunomodulators, antiviral agents, anxiolytic sedatives (hypnotics and neuroleptics), beta-adrenoreceptor blockers, blood products and substitutes, inotropic agents cardiac agents, corticosteroids, cough suppressors (expectorants and mucolytic agents), diuretics, dopaminergics (antiparkinsonian agents), hemostatic agents, immunologic agents, lipid regulator agents, muscle relaxants, parasympathomimetics, prostaglandins, leukotriene's, bronchodilators, sexual hormones (including steroids), anti-allergic agents, sympathomimetic agents, vasodilators, prokinetic agents, anti-emetic agents, chemotherapic agents, and xanthines.

In some embodiments, the invention comprises the use of the smooth muscle tone modulating peptides for the treatment of diseases that benefit from the modulation of the smooth muscle contractility including, but not limited to: erectile dysfunction (ED), female sexual dysfunction (FSD), benign prostate hyperplasia (BPH), Raynaud's syndrome, Pulmonary Arterial hypertension (PAH), systemic arterial hypertension (SAH) and hyper-reactivity of airways associated with asthma, COPD, pulmonary fibrosis, silicosis, allergic bronchopulmonary aspergillosis, hereditary angioedema, and neonatal hypoxemic respiratory failure.

For example, a method of making a pharmaceutical composition, comprises introducing to a pharmaceutically acceptable excipient any one to more peptides above an amount sufficient to treatment of a disorder where the modulation of the tone of the smooth muscle is beneficial.

In some embodiments, the disorder is selected from the group consisting of erectile dysfunction (ED), female sexual dysfunction (FSD), benign prostatic hyperplasia (BPH), Raynaud's syndrome, pulmonary arterial hypertension (PAH), systemic arterial hypertension (SAH) and hyper-reactivity of airways related to asthma, COPD, pulmonary fibrosis, silicosis, allergic bronchopulmonary aspergillosis, hereditary angioedema, and neonatal hypoxemic respiratory failure.

In some embodiments, the peptide has an amino acid sequence of SEQ ID NO: 17, SEQ ID NO: 18, SEQ ID NO: 19, SEQ ID NO: 20, SEQ ID NO: 22, SEQ ID NO: 23, or SEQ ID NO: 24 and further wherein the disorder is PAH.

V—Application of the Smooth Muscle Tone Modulating Peptides

The smooth muscle tone modulating peptides of the present invention can be used in the treatment of diseases that benefit from modulation of the smooth tone muscles. In a particular aspect, the peptides of the present invention are applicable to the treatment of diseases in which there is an imbalance, either permanent or transient, of the smooth muscle tone.

In some embodiments, a method for treating a disorder in a patient in need of modulation of the tone of smooth muscle, comprises administering to the patient a therapeutically effective amount of any one or more peptide above.

In some embodiments, the disorder is selected from the group consisting of erectile dysfunction (ED), female sexual dysfunction (FSD), benign prostatic hyperplasia (BPH), Raynaud's syndrome, pulmonary arterial hypertension (PAH), systemic arterial hypertension (SAH) and hyper-reactivity of the airways associated to asthma, COPD, pulmonary fibrosis, silicosis, allergic bronchopulmonary aspergillosis, hereditary angioedema, and neonatal hypoxemic respiratory failure.

In some embodiments, the peptide has an amino acid sequence of SEQ ID NO: 17, SEQ ID NO: 18, SEQ ID NO: 19, SEQ ID NO: 20, SEQ ID NO: 22 SEQ ID NO: 23, or SEQ ID NO: 24 and further wherein the disorder is PAH.

The clinical conditions that follow exemplify, non-exhaustively, the possible therapeutic applications of the peptides in question.

A) ED: The relaxation of the smooth muscles of the corpus cavernosum of the penis is a common event in the mechanisms of action of the pharmacological classes most applied in the treatment of ED. For example, the PDE5i (e.g. sildenafil and tadalafil) prevent the degradation of the cyclic guanosine monophosphate (cGMP) produced by guanylate cyclase upon activation by NO and enhance the relaxation of the corpus cavernosum of the penis, thus promoting or potentiating the erection. However, PDE5i require a stimulus capable of inducing NO release from the penile nerve and the endothelium of the local vessels. Therefore, PDE5i are ineffective in patients with nerve or endothelial injuries, such as those with hypertension, diabetes or those who have undergone prostatectomy with further nerve impairment (SHAMLOUL, R.; GHANEM, H. Erectile dysfunction. *The Lancet*, 381(9861): 153-165, 2013). The peptides of the present invention promote the relaxation of the smooth muscle tissues even in the presence of nerve or endothelial injury. Therefore, the said peptides may be fully applicable to the treatment of ED, including the phenotypes resistant to PDE5i. Furthermore, the mechanism of action of the smooth muscle tone modulating peptides favors the synergistic action with PDE5i, allowing clinical co-administration.

B) FSD: FSD may be related to vascular damage in the arterial network that permeates the vagina and the clitoris, this latter constituting a key structure for the promotion of the female orgasm. Because of the anatomical similarity with the penis, it is known that the clitoris also tumesces in response to sexual stimuli through NO-dependent mechanisms (PARK, K., GOLDSTEIN, I., ANDRY, C., SIROKY, M. B., KRANE, R. J., AZADZOI, K. M. Vasculogenic female sexual dysfunction: the hemodynamic basis for vaginal engorgement insufficiency and clitoral erectile insufficiency. *International Journal of Impotence Research*, 9, 27-38, 1997). Furthermore, the vasodilation and the consequent increase of local blood flow favor the lubrication and the perception of pleasure (VELTEN, J., CHIVERS, M. L., BROTTO, L. A. Does Repeated Testing Impact Concordance Between Genital and Self-Reported Sexual Arousal in Women? *Archives of Sexual Behavior.* 47(3): 1-10. 2018). Thus, the peptides of the present invention can be used in the treatment of FSD.

C) BPH: The augmentation of the prostate that characterizes the BPH causes an increase of pressure within the urethra, hindering the outflow of urine. Eventually, the urinary obstruction is total, causing the event of Acute Urinary Retention, an acute complication of BPH. The treatment of Acute Urinary Retention is also based on mechanisms of action capable of causing the relaxation of the urethral smooth muscle thus reducing the intra-urethral pressure (THOMAS, K., CHOW, K., KIRBY, R. S. Acute urinary retention: a review of the aetiology and management. *Prostate cancer and prostatic diseases*, 7(1): 32. 2004). In view of the activity of the peptides of the present invention on the smooth muscles, it is expected that they might be applied to the treatment of BPH.

D) PAH: PAH is a rare serious chronic cardiopulmonary disease caused by cellular proliferation and fibrosis of the small pulmonary arteries, with particular hyperplasia and hypertrophy of the smooth muscle cells. As a result of structural alterations, PAH is clinically identified by a progressive increase in pulmonary vascular resistance. The current therapeutic options for PAH target essentially three signaling pathways: prostacyclin, endothelin-1 and NO. All of those pharmacological classes regulate the vasomotor tone, promoting relaxation of the vessels and reduction of the vascular resistance (LAU, E. M. T., GIANNOULATOU, E., CELERMAJER, D. S., HUMBERT, M. Epidemiology and treatment of pulmonary arterial hypertension. *Nature Reviews Cardiology,* 14(10):603-614. 2017). PAH was further subdivided by the World Health Organization in five groups according to its etiology. The biggest group is group 1 PAH, that comprises idiopathic PAH (iPAH), heritable PAH, drug, and toxin-induced PAH, PAH associated with other diseases, and persistent pulmonary hypertension of the newborn (PPHN). Among these, iPAH has the greatest incidence. (CHESTER, A. H., YACOUB, M. H., MONCADA, S. Nitric oxide and pulmonary arterial hypertension. *Global Cardiology Science and Practice,* 14. 2017). PAH was already shown to be associated with strong systemic inflammation, with patients showing elevated levels of circulating inflammatory cytokines, including IL-1β, IL-6, IL-8, TNF-α, among others (PRICE, L. C., WORT, S. J., PERROS, F., DORFMULLER, P., HUERTAS, A., MONTANI, D., COHEN-KAMINSKY, S., HUMBERT, M. Inflammation in pulmonary arterial hypertension. *CHEST,* 141(1):210-221. 2012). The peptides of the present invention can be employed for the treatment of PAH since they are able to promote the vasodilation of pulmonary arteries, reduce pulmonary artery pressure, improve PAH-related secondary cardiovascular alterations, and reduce inflammation.

E) SAH: the pathological increase of the blood pressure results in the deregulation of the cardiac debt and/or of the peripheral vascular resistance. Currently available therapeutic approaches target one or both components of the blood pressure. Different pharmacological classes are employed to reduce the peripheral resistance, however a great part of them promote the relaxation of the smooth muscles of vessels or blocks the action of contractile stimuli (for example, those emitted by the sympathetic ANS) (see GOODMAN, L. S. and GILMAN, A. Goodman & Gilman's pharmacological basis of therapeutics. New York: McGraw-Hill. p. 846, 2006). The smooth muscle tone modulating peptides described in the present invention are able to relax vascular structures and improve cardiovascular features secondary to hypertension, and therefore may be useful in the treatment of SAH.

F) Raynaud's Syndrome: the physiopathology of the disease is characterized by ischemic spasms in the extremity of the hands, triggered by cold or emotional stress. The suggested treatment is based on the reversion of the local vasoconstriction, with topical application of vasodilator substances such as nitrates, PDE5i, calcium channel blockers and prostaglandins (BAUMHAKEL, M., BOHM M. Recent achievements in the management of Raynaud's phenomenon. *Vasc Health Risk Manag.* 6: 207-214. 2010). Therefore, the peptides of the present invention, that are capable of promoting the relaxation of the smooth muscles and subsequent vasodilation, can be applied in the prevention and treatment of Raynaud's disease.

G) Airway hyperreactivity: The expression "hyperreactivity" denotes an increase in the contractile of the airways in the face of a constrictor stimulus. That phenomenon is common in various diseases of the respiratory system, among which there may be pointed out asthma, COPD, bronchitis, allergic rhinitis, and others. The hyperreactivity of the airways is mediated by the soft muscle tissue layer that coats the upper airways and extends to the bronchioles. The treatment involves the asymptomatic control of the inflammatory processes that lead to the hyperreactivity of the airways, however, the recovery from crises is performed with bronchodilators, that promote the relaxation of the adjacent smooth muscles (see BRAMAN, S. S., BARROWS, A. A., DECOTIIS, B. A., SETTIPANE, G. A., CORRAO, W. M. Airway hyperresponsiveness in allergic rhinitis: a risk factor for asthma. *Chest,* 91(5): 671-674. 1987; POSTMA, D. S., and KERTJENS, H. A. M. Characteristics of airway hyperresponsiveness in asthma and chronic obstructive pulmonary disease. American journal of respiratory and critical care medicine, 158(supplement_2): S187-192, 1998; INMAN, M. D. Airway hyperresponsiveness. *CHEST Journal,* 123(3): 411S-416S. 2003). The peptides of the present invention reverted the contraction of the airways induced by a spasmodic stimulus, without triggering an inflammatory response, and thereby such substances may be used to treat, at least, the symptomatology of diseases of the respiratory system with an inflammatory component, examples of which are asthma and COPD.

H) Interstitial Lung Diseases (Pulmonary Fibrosis): Pulmonary fibrosis is one of the subtypes of interstitial lung disease. These diseases are characterized by intense fibroproliferation in consequence of a lung injury that is followed by an inflammatory process, and then the aforementioned fibroproliferation and fibrosis (REYNOLDS, H. Y. GAIL, D. B., KILEY, J. P. Interstitial pulmonary disease—where we started from and are now going. *Sarcoidosis Vasc. Diffuse Pulm. Dis.,* 22(1):5-12). It is described in the earlier literature that an increase in iNOS expression is noted in the pathogenesis of the disease and thought to be an important marker of disease progression (2005; HSU Y. C., WANG, L. F., CHIEN, Y. W. Nitric oxide in the pathogenesis of diffuse pulmonary fibrosis. *Free Radic Biol Med,* 42(5):599-607, 2007). Later data using mice knockout for the three NOS isoforms and subjected to bleomycin treatment, an experimental way to induced pulmonary fibrosis in animals, found that the mice knockout for the three isoforms have worse prognosis than healthy animals, therefore the peptide compositions of the present invention have the potential to act on the underlying inflammation and currently unknown factors, being a candidate for use in the treatment of pulmonary fibrosis (NOGUCHI, S., YATERA, K., WANG, K. Y., ODA, K., AKATA, K., YAMASAKI, K., KAWANAMI, T., ISHIMOTO, H., TOYOSHIRA, Y., SHIMOKAWA, H., YANAGIHARA, N., TSUTSUI, M., MUKAE, H. Nitric oxide exerts protective effects against bleomycin-induced pulmonary fibrosis in mice. *Respir Res,* 15(1); 92; 2014).

I) Silicosis: Occupational exposure to crystalline silica dust can result in silicosis, a chronic pulmonary disease. Once the silica particles are inhaled they trigger persistent inflammation of the alveoli and pulmonary fibrosis (THAKUR A. S., BEAMER C. A., MIGLIACCIO C. T., HOLIAN A. Critical of MARCO on crystalline silica-induced pulmonary inflammation. *Toxicol. Sci.* (108): 462-471; 2009). The silica particles induce macrophage activation, resulting in increased recruitment of neutrophils, lymphocytes, and fibroblasts, the cause of the resulting fibrosis. As of the time of this writing, there is no effective treatment to either treat the lung fibrosis or alter the progressive course of the disease (GREENBERG M. I., WAKSMAN J., CURTIS J. (2007). Silicosis: a review. *Dis. Mon.* (53):394-416; 2007; LEUNG, C. C., YU, I. T., CHEN, W. Silicosis. *Lancet,* 379(9830):2008-2018; 2012; CARNEIRO, P. J., CLEVELARIO, A. L., PADILHA, G. A., SILVA, J. D., KITOKO, J. Z., OLSEN, P. C., CAPELOZZI, V. L., ROCCO, P. R., CRUZ, F. F. Bosutinib Therapy Ameliorates Lung Inflammation and Fibrosis in Experimental Silicosis. *Front Physiol.* 2017 Mar. 15; 8:159. 2017). The bronchodilator effect of the present invention, secondary to smooth muscle cell relaxation in tracheal rings is useful for symptomatic patients with airflow obstruction, without causing an increase in lung tissue inflammation.

J) Allergic bronchopulmonary aspergillosis (ABPA): ABPA is a pulmonary disorder characterized by a hypersensitivity reaction to *Aspergillus fumigatus* in patients with asthma and cystic fibrosis. It presents with uncontrolled asthma and recurring pulmonary infiltrates, leading to wheezing, hemoptysis, productive cough, low grade fever, weight loss, malaise, and fatigue (AGARWAL, R. CHAKRABARTI, A., SHAH, A., GUPTA, D., MEIS, J. F., GULERIA, R., MOSS, R., DENNING, D. W., and For the ABPA complicating asthma ISHAM working group. Allergic bronchopulmonary aspergillosis: review of literature and proposal of new diagnostic and classification criteria. *Clinical Et Experimental Allergy*, (43):850-873, 2013). In patients with cystic fibrosis that have high risk of also developing ABPA, exhaled nitric oxide is lower than in patients with low risk, suggesting that iNOS is down-regulated by the *Aspergillus* toxin (LIM, A. Y., CHAMBERS, D. C., AYRES, J. G., STABLEFORTH, D. E., HONEYBOURNE, D. Exhaled nitric oxide in cystic fibrosis patients with allergic bronchopulmonary aspergillosis. *Respir Med.* 97(4):331-6, 2003). Moreover, the bronchodilator effect of the present invention, secondary to smooth muscle cell relaxation in tracheal rings is useful for patients with airflow obstruction, without causing an increase in lung tissue inflammation.

L) Neonatal hypoxemic respiratory failure: this is a neonatal condition that could benefit from the present invention. Persistent pulmonary hypertension of the newborn (PPHN) is a failure of normal pulmonary vascular adaptation at birth or soon after, resulting in high pulmonary vascular resistance. Therapies for PPHN are aimed at lowering pulmonary vascular resistance, with different modalities of mechanical respirators being employed for this end. In case of failure intravenous vasodilators (tolazoline, epoprostenol, and enoximone) and PDE5i are used. However, these compounds have an adverse risk profile, being known to cause hypotension, renal failure, and hemorrhage in some patients. Inhaled nitric oxide administration has a better safety profile for this group of patients, however the suboptimal lung inflation of these patients compromises the potential results (MURACA, M. C., NEGRO, S., SUN, B., BUONOCORE, G. Nitric oxide in neonatal hypoxemic respiratory failure. *The Journal of Maternal-Fetal and Neonatal Medicine,* 25(S(1)): 47-50. 2012). The peptides described in this invention can have a better safety profile, due to the absence of systemic exposure when administered intranasally through an appropriate device or inhaler, and have the potential to be more efficient than inhaled nitric oxide, owing to the fact that the peptides of the current invention are able to induce the expression of NOS isoforms, therefore generating locally available NO.

Therefore, the invention also contemplates the use of the smooth muscle tone modulating peptides to treat individuals suffering from the above-mentioned condition.

The invention also contemplates the use of the smooth muscle tone modulating peptides in the preparation of a medicament for the treatment of the above-mentioned diseases.

The biological activity of the smooth muscle tone modulating peptides, of their analogues and derivatives, may be verified by way of different methodologies ex vivo and in vivo. The examples below describe the ex vivo relaxing activity of the smooth muscle tone modulating peptides, without triggering inflammation, in "isolated organ" models based on fragments of tracheal rings, pulmonary arteries and penile cavernosal strips, structures rich in smooth muscle tissue. Other examples below describe the in vivo effect of pulmonary arterial pressure decrease due to vasodilatation, improvement of hemodynamic parameters and anti-inflammatory effect of a selected smooth muscle tone modulating peptide in a PAH rat model, a model characterized by a cardiopulmonary disease caused by the increased pressure of pulmonary artery caused by persistent smooth muscle hypercontraction.

The invention will thus hereinafter be described by means of examples, which illustrate additionally the present invention, without it being intended, however, that these might limit the scope of the present invention.

EXAMPLES

Example 1: Synthesis of the Peptides

The peptides of the present invention were chemically synthesized by Fmoc/t-butyl synthesis in solid support, in resin Rink-amide (0.68 mmol/g) produced by the company Genone, Rio de Janeiro, Brazil (batches: P170313-TL569356, P170313-TL569357, P170313-TL569358, P170315-TL569368, P170315-TL569382, P170313-TL569361, P170315-TL569362, P170313-TL569359, P170313-TL569360, P170315-TL569363, P170315-TL569364, P170313-TL569366, P170313-TL569367, WB170023-P171025, WB170024-P171025, P170315-TL569382, P170315-TL569383, P170315-TL569384, P170315-TL569380, WB170028-P171025, P170315-TL569381, P170315-TL569385, P170315-TL569386, P170315-TL569387, P170315-TL569380, WB170017-P171025, WB170025-P171025, WB170027-P171025, WB170026-P171025 and WB170022-P171025). The final cleavage and deprotection were realized with water-TFA-1.2-ethanedithiol-triisopropyl silane, 92.5-2.5-2.5-2.5 (v/v), 25° C., 180 min. The peptides were extracted with an aqueous solution of 50% (v/v) of acetonitrile and purified by reverse-phase chromatography (RPC) in a column of Sephasil C8 peptide (5μ ST 4.6/100-HPLC), balanced with water TFA 0.1%. The samples were eluted using a gradient of acetonitrile with 0.1% de TFA, flow rate of 2 ml/min, at 280 nm. After purification, the counterion exchange from TFA for all compositions can be changed to chloride or acetate ion in order to keep all the desired physicochemical characteristics (such as solubility, pI, pK, stability, among others). Furthermore, all peptides were N-terminally acetylated and C-terminally amidated to increase the solubility.

Example 2: Relaxing Effect in Airways Muscles Ex Vivo

The magnitude of the relaxing effect of the peptides was evaluated by means of a model of spasmodic contraction of tracheal rings ex vivo, largely employed to test new bronchodilating agents (see CULLUM, V. A., FARMER, J. B., JACK, D., LEVY, G. P. Salbutamol: a new, selective β-adrenoceptive receptor stimulant. *British journal of pharmacology*, 35(1): 141-151. 1969; KAO, C. H., CHU, Y. H., WANG, H. W. Effects of lidocaine on rat's isolated tracheal smooth muscle. *European Archives of Oto-Rhino-Laryngology*, 267(5): 817-820. 2010; SORIANO-URSÚA, M. A., VALENCIA-HERNÁNDEZ, I., ARELLANO-MENDOZA, M. G., CORREA-BASURTO, J., TRUJILLO-FERRARA, J. G. Synthesis, pharmacological and in silico evaluation of 1-(4-dihydroxy-3, 5-dioxa-4-borabycyclo [4.4.0] deca-7,9, 11-trien-9-yl)-2-(tert-butylamine) ethanol, a compound designed to act as a β2 adrenoceptor agonist. *European journal of medicinal chemistry*, 44(7): 2840-2846. 2009).

For each test, Dunkin-Hartley guinea pigs (400-500 g) were euthanized in a $CO_2$ atmosphere; subsequently, the trachea was exposed, removed and sectioned in segments of 1 to 3 cartilaginous tracheal rings. Each segment was transferred to an individual organ bath system containing Krebs nutritive solution (NaCl 118 mM; KCl 4.8 nM; $CaCl_2$) 2.5 mM; $MgSO_4$ 1.2 mM; $KH_2PO_4$ 1.2 mM; $NaHCO_3$ 24 mM; glucose 11 mM) at 37° C., under constant aeration with a carbogenic mixture (95% of $O_2$ and 5% of $CO_2$). In each system, a stem fixed to the base of the container and another connected to an isometric transducer (GRASS FT-03) made up the support of the fragments. A data digitizing system connected to the isometric transducer allowed the recording of tension variations produced by the contraction of the tracheal rings (PowerLab™ 16/30, LabChart, version 8.1, AD Instruments, Australia). The basal tension was adjusted to 1 g, and subsequently, the contractility of the fragments was evaluated by a stimulus with carbachol (2.5 μM). After 1 h at rest, the basal tension was recovered and the tissues were subjected to contraction induced by histamine (50 μM) followed by exposure to increasing concentrations of the treatments (0.01 to 10 μM; n=8) or the comparator PnTx(19).

Table 1 lists the mean±SEM of the potency values, shown as the negative logarithm of the concentration that reduced the voltage to 50% of the maximum Histamine-induced contraction (pEC50), and efficacy (Emax), calculated from at least 8 independent tests using the sigmoid nonlinear regression equation of the software Graph Prism 5.0 (Graph-Pad Software, La Jolla, Ca, USA). The result obtained with the comparator PnTx(19) is shown in FIG. 1.

TABLE 1

Potency (pEC50) and efficacy values (Emax) obtained from the concentration-response curve for the active peptides in the relaxation of the smooth muscle of tracheal rings ex vivo.

| Sequences | Potency ($pEC_{50}$) Molar | Effectiveness (Emax) (%) |
|---|---|---|
| SEQ ID NO: 1 | 7.1 ± 0.4 | 45.7 ± 4.3 |
| SEQ ID NO: 2 | 6.9 ± 0.2 | 40.4 ± 2.6 |
| SEQ ID NO: 3 | 6.8 ± 0.2 | 36.7 ± 1.9 |
| SEQ ID NO: 4 | 6.8 ± 0.3 | 38.8 ± 3.5 |
| SEQ ID NO: 5 | Inactive | Inactive |
| SEQ ID NO: 6 | 7.0 ± 0.3 | 25.3 ± 1.7 |
| SEQ ID NO: 7 | Inactive | Inactive |
| SEQ ID NO: 8 | Inactive | Inactive |
| SEQ ID NO: 9 | Inactive | Inactive |
| SEQ ID NO: 10 | Inactive | Inactive |
| SEQ ID NO: 11 | Inactive | Inactive |
| SEQ ID NO: 12 | Inactive | Inactive |
| SEQ ID NO: 13 | Inactive | Inactive |
| SEQ ID NO: 14 | Inactive | Inactive |
| SEQ ID NO: 15 | Inactive | Inactive |
| SEQ ID NO: 16 | Inactive | Inactive |
| SEQ ID NO: 17 | 6.8 ± 0.3 | 37.1 ± 2.6 |
| SEQ ID NO: 18 | 7.2 ± 0.3 | 38.0 ± 2.3 |
| SEQ ID NO: 19 | 7.3 ± 0.4 | 40.0 ± 3.4 |
| SEQ ID NO: 20 | 7.1 ± 0.3 | 37.8 ± 2.9 |
| SEQ ID NO: 21 | Inactive | Inactive |
| SEQ ID NO: 22 | 7.0 ± 0.2 | 35.2 ± 1.8 |
| SEQ ID NO: 23 | 7.5 ± 0.3 | 35.5 ± 2.3 |
| SEQ ID NO: 24 | 7.9 ± 0.3 | 29.0 ± 1.0 |
| SEQ ID NO: 25 | Inactive | Inactive |
| SEQ ID NO: 26 | Inactive | Inactive |
| SEQ ID NO: 28 | Inactive | Inactive |
| SEQ ID NO: 29 | Inactive | Inactive |
| SEQ ID NO: 30 | Inactive | Inactive |

The presence of the sequence Ile-Ala-Trp as Xaa6, Xaa7, and Xaa8, respectively, is important to the biological effect of the peptide. For example, sequences SEQ ID NO: 1, SEQ ID NO: 2, SEQ ID NO: 3 and SEQ ID NO: 4 have Ile-Ala-Trp between Xaa5 and Xaa9, and therefore are effective in relaxing smooth muscle cells of airways muscles. However, sequence SEQ ID NO: 7 have Ala instead of Ile as Xaa6, and sequence SEQ ID NO: 8 have Ala instead of Trp as Xaa8, and therefore both are inactive. In the same way, the sequence SEQ ID NO: 24 also has Ile-Ala-Trp as Xaa6, Xaa7, and Xaa8, respectively, and is effective in relaxing the tracheal rings smooth muscle. However, SEQ ID NO: 26 have Tyr instead Trp in Xaa8 position and therefore is inactive.

Another aspect for the biological activity of the described peptides is that Xaa1, Xaa2, and Xaa15 either are independently absent, or are an Ala, or are basic natural amino acid (Arg, Lys or His). For example, comparing with the active sequence of peptide SEQ ID NO: 1, SEQ ID NO: 2, SEQ ID NO: 3 and SEQ ID NO: 4, the sequence SEQ ID NO: 15 have Glu, an acidic amino acid in position Xaa1, instead of a basic amino acid, and therefore is inactive. In the same way, sequence SEQ ID NO: 16 have Glu in position Xaa15, instead of basic amino acid, and therefore is also inactive.

Another aspect for the biological activity of the described peptides is that each of Xaa4, Xaa5, and Xaa9 is independently absent or is an aromatic amino acid (Phe, Trp or Tyr). For example, the sequences SEQ ID NO: 9, SEQ ID NO: 10 and SEQ ID NO: 11 have in the position Xaa4, Xaa5, and Xaa9, respectively, Ala, a non-aromatic amino acid, instead of an aromatic amino acid (Phe, Trp or Tyr) as the active sequence of peptide SEQ ID NO: 1, SEQ ID NO: 2, SEQ ID NO: 3 and SEQ ID NO: 4, and therefore they are inactive.

Another aspect for the biological activity of the described peptides is that Xaa10 is independently absent or is a basic natural amino acid (Arg, Lys, His). For example, comparing with the active sequence of peptide SEQ ID NO: 1, SEQ ID NO: 2, SEQ ID NO: 3 and SEQ ID NO: 4, the sequence SEQ ID NO: 12 has Ala, a nonpolar amino acid, instead of a basic amino acid, and therefore are inactive.

Another aspect of the biological activity of the described peptides is that Xaa12 is either absent or Ala. For example, when compared with SEQ ID NO: 19, SEQ ID NO: 21 have Leu instead of Ala in position Xaa12 and therefore is inactive.

Another aspect for the biological activity of the described peptides is that each of Xaa13 and Xaa14 is independently absent or is an uncharged polar amino acid (Asn, Gln, Ser or Thr). For example, the sequences SEQ ID NO: 13, and SEQ ID NO: 14 have Ala, a nonpolar amino acid in the position Xaa13 and Xaa14, respectively, instead of an uncharged polar amino acid as the active sequence of peptide SEQ ID NO: 1, SEQ ID NO: 2, SEQ ID NO: 3 and SEQ ID NO: 4, and therefore they are inactive.

Example 3: Relaxing Effect in Cavernosal Strips Ex Vivo

The relaxing potential of the peptides of the present invention on the smooth muscles of cavernous strips was evaluated ex vivo using tissue isolated from rats, a model that is largely used to test drug candidates for the treatment of ED (ITALIANO, G., CALABRÒ, A., PAGANO, F. A simplified in vitro preparation of the corpus cavernosum as a tool for investigating erectile pharmacology in the rat. *Pharmacological research,* 30(4): 325-334. 1994; GEMALMAZ, H., WALDECK, K., CHAPMAN, T. N., TUTTLE, J.

B., STEERS, W. D., ANDERSSON, K E. In vivo and in vitro investigation of the effects of sildenafil on rat cavernous smooth muscle. *The Journal of Urology*, 165(3): 1010-1014.2001).

Male rats of Sprague Dawley (SD) lineage were sacrificed by guillotine; the penises were removed surgically and placed on a Petri dish containing Krebs—bicarbonate solution (NaCl 118.1 mM; KCl 4.7 mM; $KH_2PO_4$ 1.0 mM; $MgSO_4$ 1.0 mM; $NaHCO_3$ 25.0 mM; $CaCl_2$) 2.5 mM and Glucose 11.1 mM). The corpus cavernosum were dissected by removing the glans, urethra, spongeous body and dorsal vein, and then separated by cutting the fibrous septum between them. Cavernosal strips measuring 2×2×7 mm were mounted separately in a bath for isolated organs containing bicarbonate solution-Krebs (pH 7.4) at 37° C., aerated with 95% of $O_{O2}$ and 5% of $CO_2$. The tissue was connected to a tension transducer and the changes in tension were continuously registered. The cavernosal strips were contracted with phenylephrine ($10^{-5}$ M) and subsequently relaxed by electrical stimulation at different frequencies (1 to 32 Hz). The stimulation occurred after 10 minutes of incubation with different concentrations of the peptides SEQ ID NO: 5, SEQ ID NO: 8, SEQ ID NO: 19 and SEQ ID NO: 24 ($10^{-10}$ M; $10^{-8}$ M; $10^{-6}$ M), demonstrated for the sake of explanation, in the presence or absence of L-NAME, an unspecific NOS blocker. Alternatively, the peptides were substituted by the comparator PnTx(19) in single concentration ($10^{-8}$M), n=6. Differences in the percentage of relaxation between treatment and control were evaluated with regard to statistical significance by means of two-way variance analysis (Two-Way ANOVA) followed by Bonferroni post-test. For the comparison between the treatments and control in light of the stimulation in a single frequency, the results were evaluated by one-way analysis variance (One-Way ANOVA) followed by Bonferroni post-test. In all cases, the results were considered statistically distinct for all values p lower than 0.05.

Figure 2:
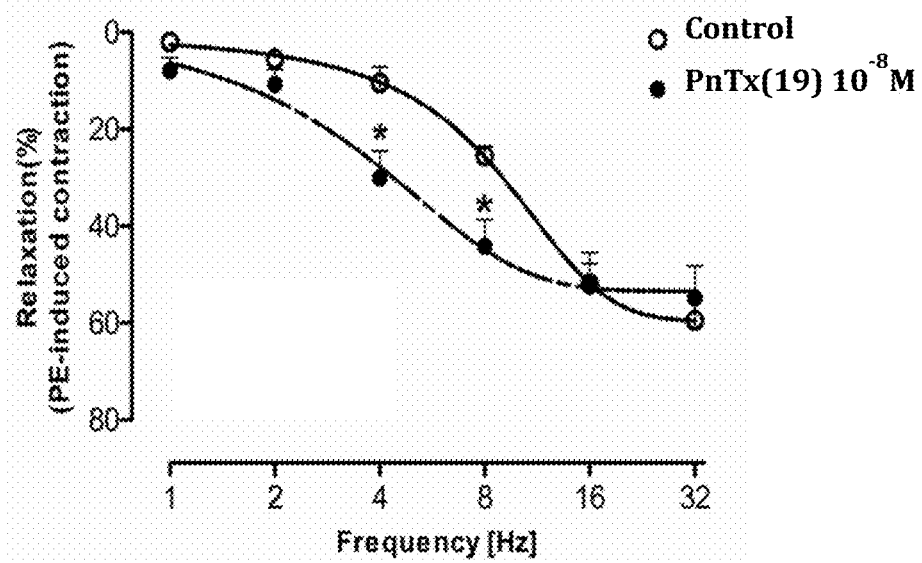
FIG. 2 shows the enhancing effect of PnTx(19) ($10^{-8}$ M) on the relaxation induced by electric stimuli in strips of cavernous bodies pre-contracted with phenylephrine ex vivo. The graph shows the mean±SEM of the results obtained with 6 cavernosal strips from different animals.
Figure 3:
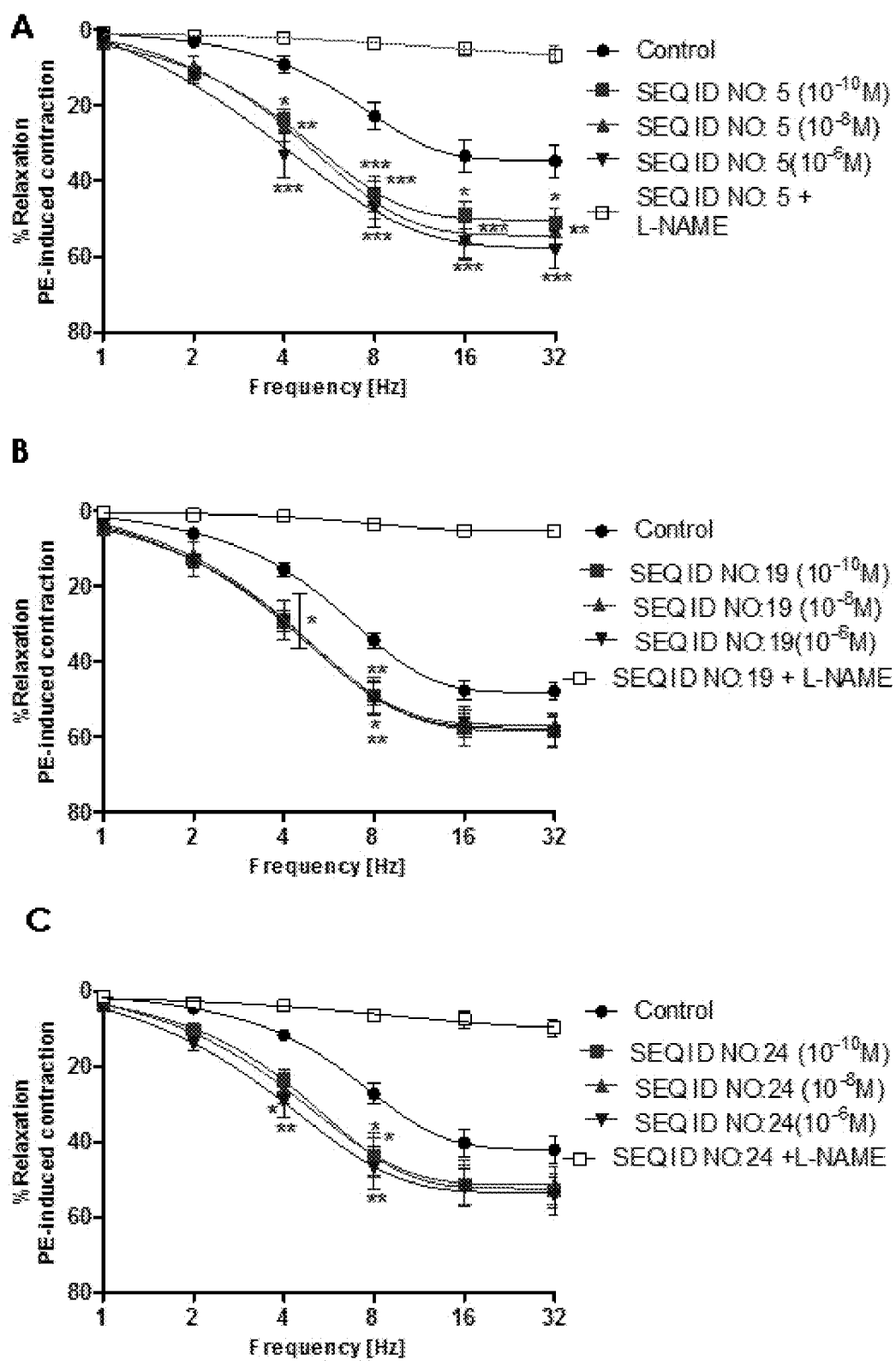
FIG. 3 shows the enhancing effect ex vivo of smooth muscle tone modulating peptides on the relaxation induced by electric stimuli in strips of cavernous body contracted by phenylephrine (PE). The peptides SEQ ID NO: 5 (A), SEQ ID NO: 19 (B), and SEQ ID NO: 24 (C) were evaluated in an exemplary mode in the model in question. The graphs show the mean±SEM of the results obtained with 6 cavernosal strips from different animals.
Figure 4:
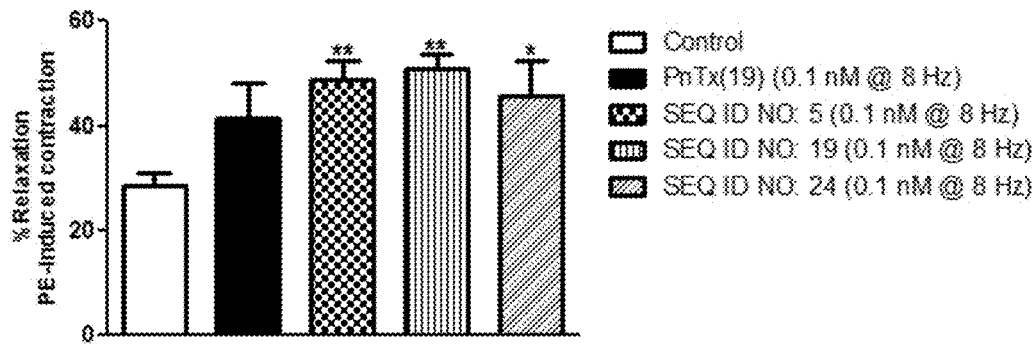
FIG. 4 shows the effect ex vivo of the comparator PnTx(19) ($10^{-8}$ M) and the smooth muscle tone modulating peptides on the relaxation induced by electric stimuli (8 Hz) in strips of cavernous bodies pre-contracted by phenylephrine (PE). The graph shows the mean±SEM of the results obtained with at least 6 strips of cavernous bodies extracted from different animals. The difference between the groups was analyzed by one-way analysis of variance (One-Way ANOVA) followed by the Bonferroni post-hoc test. * indicates $p<0.05$ compared to the control; ** indicates $p<0.01$ compared to control.

As described in the art, PnTx(19) is effective in potentiating the smooth muscle relaxation promoted by the electric stimulus on precontracted cavernous strips (FIG. 2). However, the smooth muscle tone modulating peptides of the present invention potentiated the electric stimulation-induced relaxation of cavernosal strips at a concentration as low as $10^{-16}$M (FIG. 3). Therefore, in comparison with PnTx(19), the peptides of this invention are at least 100 times more potent ($10^{-10}$M vs $10^{-8}$M), when compared at the optimal stimulatory frequency range (FIG. 4). However, in the presence of L-NAME, an unspecific NOS blocker, the peptides of the present invention were unable to promote the relaxation of the smooth muscles of cavernous bodies, indicating that the therapeutic effect of the compounds described herein is mediated by NO.

Although the invention was described with regard to particular modalities, it will be visible for those skilled in the art that various modifications and variations might be made therein without deviating from the scope and the spirit of the present invention.

Example 4: Relaxing Effect in Pulmonary Arteries Ex Vivo

The ex vivo model of pulmonary artery smooth muscle contraction with phenylephrine is very useful to screen candidate compounds for lung diseases that demand vasodilating effects (ALENCAR, A. K., PEREIRA, S. L., MONTAGNOLI, T. L., MAIA, R. C., KUMMERLE, A. E., LANDGRAF, S. S., CARUSO-NEVES, C., FERRAZ, E. B., TESCH, R., NASCIMENTO, J. H., DE SANT'ANNA, C. M., FRAGA, C. A., BARREIRO, E. J., SUDO, R. T., ZAPATA-SUDO, G. Beneficial effects of a novel agonist of the adenosine A2A receptor on monocrotaline-induced pulmonary hypertension in rats. *Br J Pharmacol*, 169: 953-62. 2013).

Since this vasodilation can be achieved via NO producing compounds, the extent of the applications in relaxing smooth muscle from different tissues was demonstrated in an ex vivo assay using male Wistar rats pulmonary arteries. Rats were anesthetized with midazolam and ketamine (2 mg/kg and 100 mg/kg, respectively) via intraperitoneal administration. After infusion of a lethal dose of sodium thiopental via intraperitoneal administration (50 mg/kg), the trunk of the pulmonary artery was carefully removed via sternotomy. The pulmonary artery was carefully dissected and the connective tissue removed. The arteries were connected to a force transductor, positioned in vertical chambers filled with Krebs solution, oxygenated and kept at 37° C.

After a stabilization period of 2 hours at a tension of 1.5 grams, the arteries were exposed to increasing doses of phenylephrine (1 nM-10 μM) in order to obtain maximum smooth muscle contraction and then exposed to increasing doses of selected peptides in the concentrations of 1 nM-10 μM each (n=9). The tension generated by the pulmonary artery was evaluated at intervals of 5 minutes for each dose (ALENCAR, A. K., PEREIRA, S. L., MONTAGNOLI, T. L., MAIA, R. C., KUMMERLE, A. E., LANDGRAF, S. S., CARUSO-NEVES, C., FERRAZ, E. B., TESCH, R., NASCIMENTO, J. H., DE SANT'ANNA, C. M., FRAGA, C. A., BARREIRO, E. J., SUDO, R. T., ZAPATA-SUDO, G. Beneficial effects of a novel agonist of the adenosine A2A receptor on monocrotaline-induced pulmonary hypertension in rats. *Br J Pharmacol* 169: 953-62. 2013; ALENCAR, A. K., PEREIRA, S. L., DA SILVA, F. E., MENDES, L. V., CUNHA VDO, M., LIMA, L. M., MONTAGNOLI, T. L., CARUSO-NEVES, C., FERRAZ, E. B., TESCH, R., NASCIMENTO, J. H., SANT'ANNA, C. M., FRAGA, C. A., BARREIRO, E. J., SUDO, R. T., ZAPATA-SUDO, G. N-acylhydrazone derivative ameliorates monocrotaline-induced pulmonary hypertension through the modulation of adenosine AA2R activity. *International Journal of Cardiology*, 173(2): 154-62. 2014). Arteries that did not achieve any contraction with phenylephrine were excluded from this assay.

The results of the assay are summarized below, at table 2. Potency values are shown as the negative logarithm of the concentration that reduced the voltage to 50% of the maximum phenylephrine-induced contraction (pEC50), and they are expressed as mean±SEM. The maximum contraction achieved in a given artery was considered to be 100% of contraction, and the effectiveness (Emax) was expressed as the relaxation percentage related to this maximum value. The results were calculated from at least 3 independent tests using the sigmoid non-linear regression equation, and the statistical analysis of the concentration curve was done by performing a nonlinear fit of the logarithmic of the agonist versus response. All the above calculations were performed on the software Graph Prism 5.0 (GraphPad Software, La Jolla, Calif., USA). Tension analysis was performed on the software LabChart7 (AD Instruments, Sydney, Australia). As a cutoff to determine biological significance, we considered pulmonary artery relaxation values above 30% as biologically relevant, considered those as active and then calculated the Emax values (SUN, C. K., LIN, Y. C., YUEN, C. M., CHUA, S., CHANG, L. T., SHEU, J. J., LEE, F. Y., FU, M., LEU, S., YIP, H. K. Enhanced protection against pulmonary hypertension with sildenafil and endothelial progenitor cell in rats. *International journal of cardiology*, 162(1): 45-58. 2012; ALENCAR, A. K., PEREIRA, S. L., DA SILVA, F. E., MENDES, L. V., CUNHA VDO, M., LIMA, L. M., MONTAGNOLI, T. L., CARUSO-NEVES, C., FERRAZ, E. B., TESCH, R., NASCIMENTO, J. H., SANT'ANNA, C. M., FRAGA, C. A., BARREIRO, E. J., SUDO, R. T., ZAPATA-SUDO, G. N-acylhydrazone derivative ameliorates monocrotaline-induced pulmonary hypertension through the modulation of adenosine AA2R activity. *International Journal of Cardiology*, 173(2): 154-62. 2014).

TABLE 2

Potency ($pEC_{50}$) and efficacy values ($E_{MAX}$) obtained from the concentration-response curve for the active peptides in the relaxation of the smooth muscle of pulmonary arteries ex vivo (n = 9).

| Sequences | $pEC_{50}$ | Effectiveness (Emax) (%) |
|---|---|---|
| SEQ ID NO: 17 | 7.8 ± 3.0 | 15% ± 2.6 |
| SEQ ID NO: 18 | 6.5 ± 9.3 | 18% ± 9.12 |
| SEQ ID NO: 19 | 6.9 ± 6.55 | 24% ± 9.71 |
| SEQ ID NO: 20 | 6.1 ± 6.9 | 6% ± 7.64 |
| SEQ ID NO: 22 | 5.8 ± 3.1 | 8% ± 2.83 |
| SEQ ID NO: 23 | 6.1 ± 6.2 | 4% ± 6.07 |
| SEQ ID NO: 24 | 4.4 ± 6.4 | 5% ± 5.96 |

All the peptides tested had absolute values of pulmonary arteries relaxation greater than 30%, and therefore all of them had some degree of effectiveness. SEQ ID NO: 19 was selected for further in vivo experiments due to its high effectiveness value.

Example 5: SEQ ID NO: 19 Induces Restoration of Hemodynamic Parameters In Vivo in a Monocrotaline-Induced Model of Pulmonary Arterial Hypertension (PAH)

The monocrotaline (MCT) model is the most widely used animal model of PAH, being the oldest in existence and best described among the available models. This model offers the advantage of mimicking several key aspects of human PAH, including vascular remodeling, proliferation of smooth muscle cells, endothelial dysfunction, up-regulation of inflammatory cytokines, and right ventricle failure, after a single intraperitoneal or subcutaneous MCT injection (GOMEZ-ARROYO, J. G., FARKAS, L., ALHUSSAINI, A. A., FARKAS, D., KRASKAUSKAS, D., VOELKEL, N. F., BOGAARD, H. J. The Monocrotaline Model of Pulmonary Hypertension in Perspective. *Am J Physiol Lund Cell Mol Physiol*, 302(4): L363-9. 2012).

The currently preferred species for the study of MCT-induced PAH is the rat, with clinical signs of the illness manifesting in 3-7 days after the MCT injection in the form of anorexia, listlessness, failure to gain weight, and tachypnea. As the lung injury and vascular remodeling progress, the animals develop variable degrees of dyspnea, weakness, diarrhea and peripheral cyanosis (SCHOENTAL R., HEAD, M. A. Pathological changes in rats as a result of treatment with monocrotaline. *Br J Cancer*, 9(1):229-37. 1955). One week after the MCT injection, endothelial damage, inflammatory infiltration, and edema can be observed, but no increase in pulmonary arterial pressure (PAP). After two weeks, PAP is increased leading to right ventricle (RV) hypertrophy by the third week after drug administration (WEST, J., HEMMES, A. Experimental and transgenic models of pulmonary hypertension. *Compr Physiol*, 1(2): 769-82. 2011).

To assess the potential benefit of SEQ ID NO: 19 in the treatment of PAH, we used adult healthy male Wistar Rats, which were then randomized into two groups: monocrotaline-induced PAH (MCT, n=14), in which animals received 60 mg/kg of MCT intraperitoneally (C2401, Sigma Chemical Co., St Louis, Mo., USA, Batch Number: WXBC4737V) and 2) control (CTRL, n=7), in which animals received a similar volume of saline solution intraperitoneally. This would be day 0 of the study. On the same day, prior to being randomized, the animals were subjected to echocardiographic analysis to establish a baseline. On day 14, another echocardiography was done, and PAH animals were further randomized to receive intranasal saline (SAL) or SEQ ID NO: 19 (0.06 mg/kg), twice daily for 14 days. On day 28, echocardiographies were repeated, RV exit area, left ventricle (LV) area, and PAT/PET (pulmonary arterial acceleration time (PAT)/pulmonary arterial ejection time (PET) ratio). In the PAH disease, the increase of PAP leads to an increase in RV area due to the increased pressure, and a decrease in the LV area, due to a reduction in blood flow to the left ventricle. PAT/PET ratio measurement is predictive of mild to moderate PAH, and it is considered the one of the most predictive non-invasive measurement (KOSKENVUO, J. W., MIRSKY, R., ZHANG, Y., ANGELI, F. S., JAHN, S., ALASTALO, T. P., SCHILLER, N. B., BOYLE, A. J., CHATTERJEE, K., DE MARCO, T., YEGHIAZARIANS, Y. A comparison of echocardiography to invasive measurement in the evaluation of pulmonary arterial hypertension in a rat model. *Int J Cardiovasc Imaging*, 26(5):509-18. 2010). Hemodynamic parameters were measured by invasive RV catheterization, including the systolic pressure of RV (RVSP) and the dP/dt ratio (a derivative of pressure/derivative of maximum time), which is correlated to the pressure in the RV.

Figure 5:
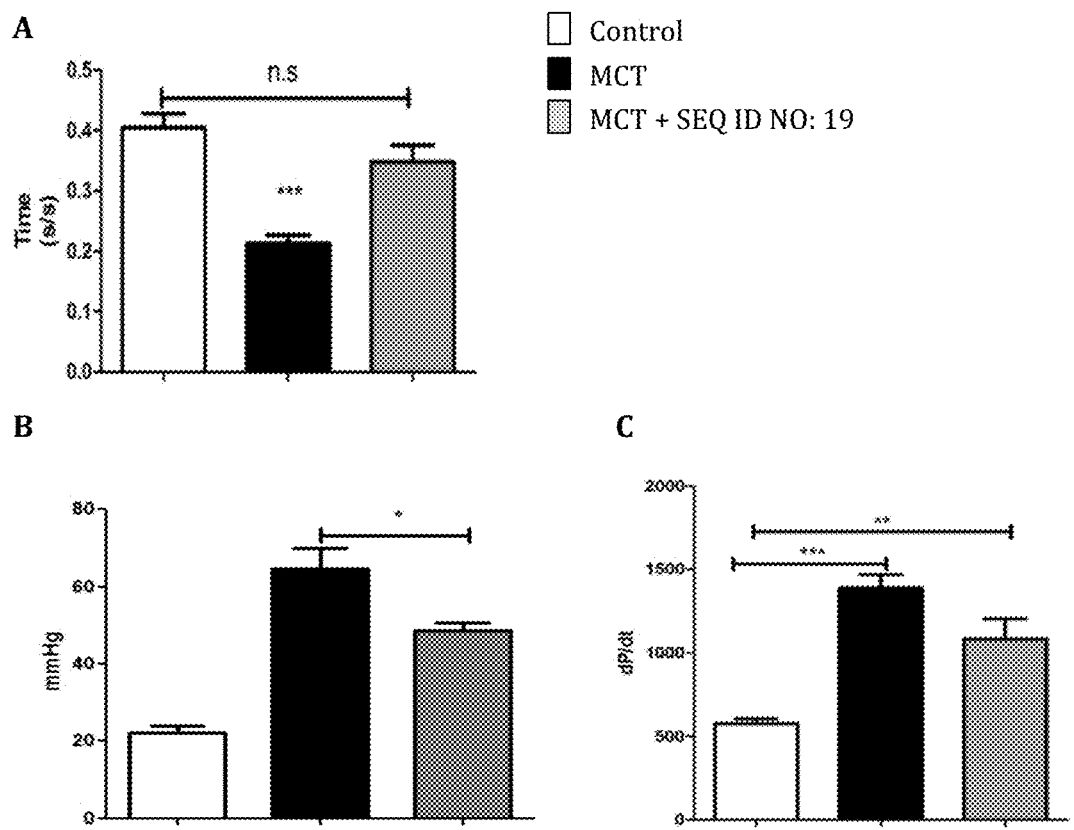
FIG. 5 shows the effect in vivo of the SEQ ID NO: 19 (0.06 mg/kg), in the restoration of pulmonary arterial pressure and consequently right ventricle (RV) pressure in a monocrotaline-induced model of pulmonary arterial hypertension (PAH), 14 days after daily treatment. The graphs show the effect of SEQ ID NO: 19 compared to a group without disease (control) and monocrotaline-induced group treated with vehicle (MCT) on (A) the PAT/PET ratio (pulmonary arterial acceleration time (PAT)/pulmonary arterial ejection time (PET) ratio), which is inversed correlated with the grade of pulmonary arterial pressure), measured by echocardiography; (B) the systolic pressure of RV (RVSP), measured by invasive RV catheterization; (C) the ratio dP/dt (derivative of pressure/derivative of maximal time), which is correlated to the pressure of the RV, measured by RV catheterization. The graphs show the mean±SEM of the results obtained with 7 different animals. The difference between the groups was analyzed by two-way ANOVA, followed by the Bonferroni post-hoc test. * indicates p<0.05;  indicates p<0.01; * indicates p<0.001; all compared to the control.
Figure 6:
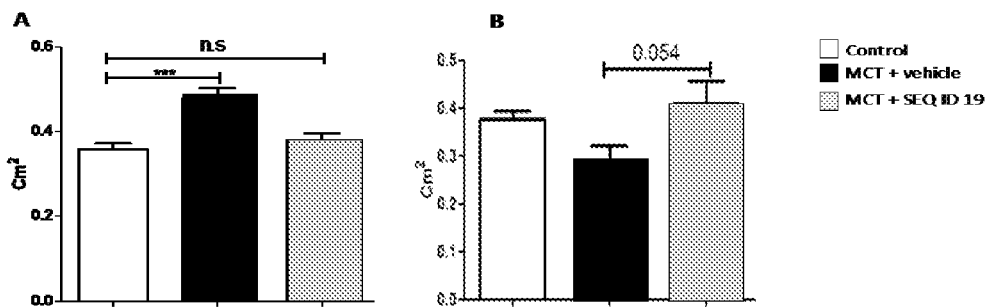
FIG. 6 shows the effect in vivo of the SEQ ID NO: 19 (0.06 mg/kg), in the heart remodeling in a monocrotaline-induced model of PAH, 14 days after daily treatment. The graphs show the effect of SEQ ID NO: 19 compared to the non-diseased group (control) and the monocrotaline-induced group treated with vehicle (MCT) on the area of (A) RV exit area, and (B) LV area. The graphs show the mean±SEM of the results obtained with 7 different animals. The difference between the groups was analyzed by two-way ANOVA, followed by the Bonferroni post-hoc test. * indicates p<0.05;  indicates p<0.01; * indicates p<0.001; all compared to the control.

The experiments were analyzed with two-way ANOVA, followed by Bonferroni's post-test to determine statistical significance. Also, depicted in the graphs of FIGS. 5 and 6 is the standard deviation between subjects.

SEQ ID NO: 19 when compared with the monocrotaline-induced group treated with vehicle (MCT+Vehicle), increases the PAT/PET ratio to values similar to the non-treated group (control), which corresponds to the reduction of PAP back to normal value range (FIG. 5A). This improvement happened after 14 days of treatment with SEQ ID NO: 19. The decrease of PAP leads to a decrease in RV pressure, demonstrated by the decrease in RVSP and in the dP/dt Max ratio in the group treated with SEQ ID NO: 19 in comparison with MCT+Vehicle group (FIGS. 5B and 5C, respectively).

The SEQ ID NO: 19 treatment also induced a decrease in RV exit area (FIG. 6A) and an increase in LV area (FIG. 6B) when compared with the MCT+vehicle group, to values similar to the control, which means that SEQ ID NO: 19 was able to remodel the heart back to normal.

These results show that besides being a vasodilating agent, SEQ ID NO: 19 could be used as a potential treatment for PAH, and other pulmonary diseases with or without an inflammatory component, as already discussed elsewhere in this manuscript.

Example 6: Anti-Inflammatory Effect In Vivo of SEQ ID NO: 19

In the experiment described in example 5, the animals were killed for postmortem analyses of inflammatory markers.

As discussed at length elsewhere in this manuscript, all pulmonary diseases, including Asthma, COPD, and PAH, present some degree of inflammation that is part of the physiopathology of the disease. A drug that is intended to treat those diseases cannot trigger inflammation, that is, be pro-inflammatory.

One of the mechanisms of the anti-inflammatory action is that smooth muscle cells relaxation can reduce endothelial permeability, and consequently reduce the migration of blood inflammatory factors, decreasing the inflammatory process (WALLACE, J. L. Nitric Oxide as a regulator of inflammatory processes. *Mem Inst Oswaldo Cruz,* 100:5-9. 2005).

Figure 7:
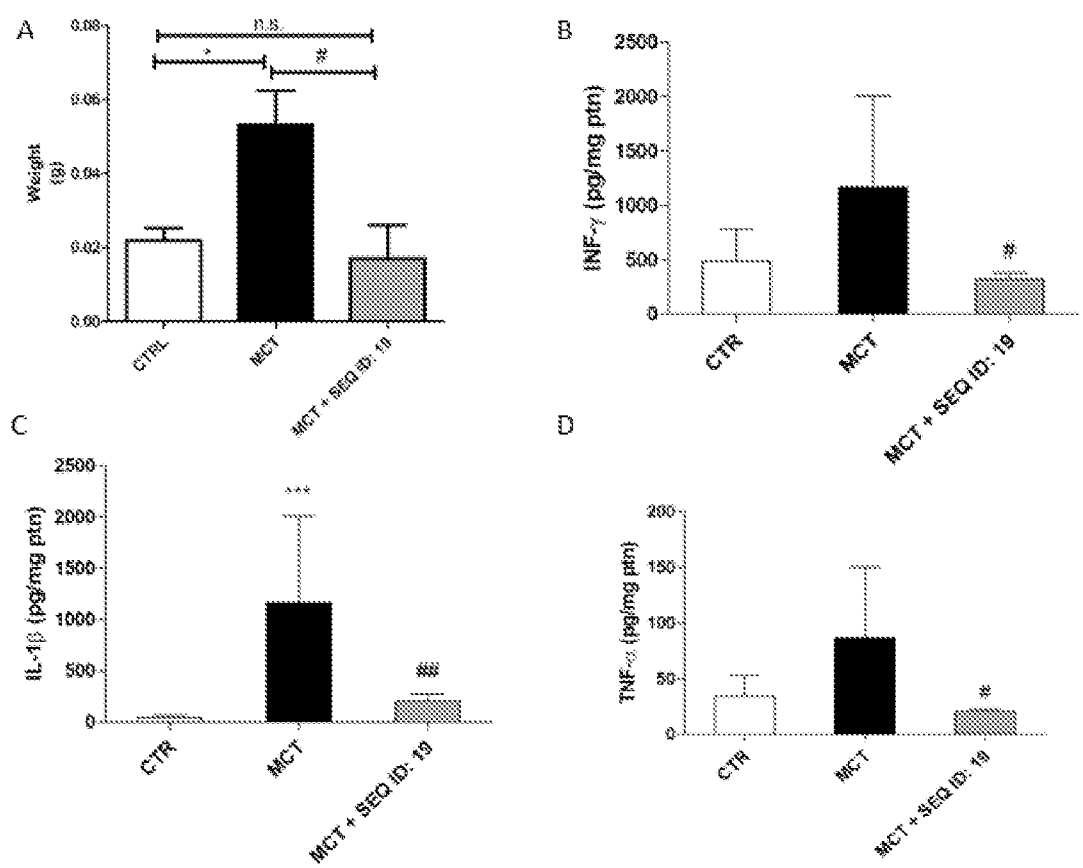
FIG. 7 shows the anti-inflammatory effect in vivo of SEQ ID NO: 19 (0.06 mg/kg), in a monocrotaline-induced model of PAH, 28 days after daily treatment. The graphs show the effect of SEQ ID NO: 19 compared to group without disease (control) and monocrotaline-induced group without treatment (MCT) on the reduction in the heart homogenates of the following pro-inflammatory cytokines release: (A) shows the effect on the prevention of mediastinal lymph node enlargement, (B) interferon (IFN)-γ, (C) interleukin (IL)-1β, represented by pg/mg of protein, measured by ELISA and on graph (D) tumor necrosis factor (TNF)-α. The graph shows the mean±SEM of the results obtained with 7 different animals. The difference between the groups was analyzed by one-way ANOVA, followed by the Bonferroni's Multiple comparison test. * and # indicates p<0.05 when compared to the control and to the MCT group, respectively; *** indicates p<0.001, and ## indicates p<0.01.

In 1 out of 5 patients with PAH, the mediastinal lymph nodes are enlarged due to inflammation-related edema (BERGIN, C. J., PARK, K. J. Lymph node enlargement in pulmonary arterial hypertension due to chronic thromboembolism. *J Med Imaging Radiat Oncol,* 52(1):18-23. 2008). Edematous organs weigh more, due to the increased liquid content, therefore we weighed several organs of the animals of example 5 post-euthanasia. SEQ ID NO: 19 treatment was able to reduce the edematous weight gain induced by the MCT treatment on mediastinal lymph nodes, making them indistinguishable from the CTRL group (FIG. 7A).

Samples of hearts of the monocrotaline study were investigated to uncover the potential anti-inflammatory action of SEQ ID NO: 19. Hearts were kept on ice during all sample homogenization processes. Lysis buffer containing 1% protease inhibitor cocktail (Sigma) diluted in phosphate-buffered saline (PBS) was added in a proportion of 1 mL for each sample. Sodium orthovanadate (SIGMA) 1 mM was also added. Tissues were homogenized and then centrifuged at 10,000 g for 10 min. Supernatants of each sample were collected into sterile identified tubes for measurements of total protein and cytokine levels (tumor necrosis factor (TNF)-α, interferon (INF)-γ, and interleukin (IL)-1β).

Total protein values in the samples were measured using the Bradford assay (BioRad, Hercules, Calif., USA), according to manufacturer's instructions. Briefly, the protocol was performed in a microplate in a final volume of 150 μl. A calibration curve linear range between 0.025 and 2.0 mg/ml was prepared with bovine serum albumin (BSA, SIGMA). Protein solutions were assayed in duplicate. Samples were diluted 20-fold into lysis buffer, and then 25 μl from these samples was loaded into each well. Using a multichannel pipet, 125 μl of Quick Start™ Bradford 1× Dye Reagent solution was added to yield a final volume of 150 μl. The samples were incubated at room temperature for 5 min, and the absorbance was then measured with a spectrophotometer at 595 nm (SpectraMax Microplate reader, Molecular Devices, San Jose, Calif., USA). The standard curve was plotted as a linear regression line that was interpolated with the mean absorbance of each sample in order to find a sample's total protein concentration expressed as mg/ml.

Concentrations of TNF-α, INF-γ, and IL-1β were measured using an enzyme-linked immunosorbent assay (ELISA) for heart homogenates. TNF-α (Catalog #900-K54) and INF-γ (Catalog #900-K98) kits were purchased from Peprotech (Rocky Hill, Colo., USA) while the IL-1β (DY401) kit was from R&D Systems (Minneapolis, Minn., USA). The assays were performed in accordance with the manufacturer's recommendations.

Data analyses were performed with a statistical software package (Prism version 5.0, Graph-Pad Software, San Diego, Calif.). Data were expressed as mean±SEM. All tests were carried out using a one-way analysis of variance (ANOVA) followed by the Bonferroni's Multiple Comparison Test. Statistical differences were considered to be significant if $p<0.05$.

In heart homogenates, MCT group showed an increase of all cytokines measured (TNF-α, INF-γ, and IL-1β), compared to the control group. SEQ ID NO: 19 decreases the cytokines to values similar to control (FIG. 7B, 7C, 7D).

Example 7: Anti-Inflammatory Effect In Vivo of SEQ ID NO: 19 and SEQ ID NO: 24 Compared to PnTX(9)

Male A/J mice (18-20 g), were sensitized by house dust mite (HDM) to established acute allergic asthma according to the protocol of Haspelagh et al (HASPESLAGH, E., DEBEUF, N., HAMMAD, H., LAMBRECHT, B. N. Murine Models of Allergic Asthma. *Methods Mol Biol,* 1559:121-136. 2017). Inflammatory cell infiltrations in the bronchoalveolar lavage fluid (BALF) were analyzed by flow cytometry.

The mice (n=5 per group) were treated with vehicle (PBS), SEQ ID NO: 19, SEQ ID NO: 24 or PnTx(19), at doses of 10 nMol and 30 nMol per animal, by intratracheal instillation, and material were collected 6 hours post-challenge.

Figure 8:
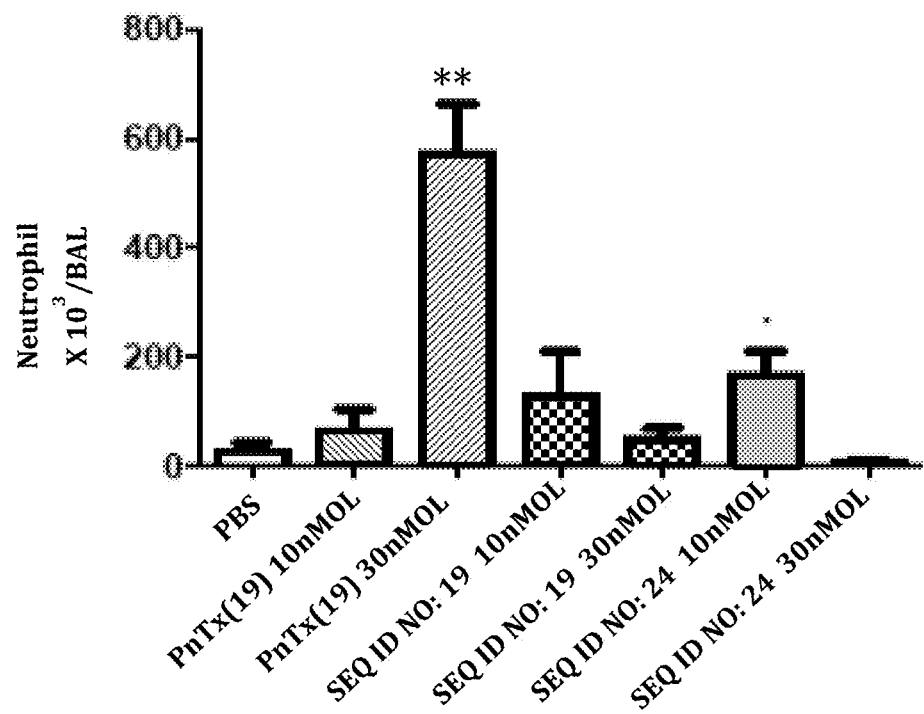
FIG. 8 shows the effect of PnTx(19), SEQ ID NO: 19, and SEQ ID NO: 24 on neutrophil migration in the bronchoalveolar space after intratracheal instillation of the peptides (10 nMol and 30 nMol) 6 h post challenge, in a murine model (n=5). The values represent the mean±SEM from at least five animals, +++ indicates p<0.001 when compared PBS-stimulated to the PBS-treated mice.

Mice exposed to PnTx(19) (30 nMol) showed a substantial increase in the total leukocyte cell numbers in the BALF, which was primarily due to the accumulation of neutrophils (FIG. 8). SEQ ID NO: 19 and SEQ ID NO: 24 treatment did not induce neutrophil accumulation in the bronchoalveolar space after 6 h of intratracheal instillation of the peptide (FIG. 8), suggesting that both peptides don't have a pro-inflammatory effect in the mice lung, unlike the comparator PnTx(19). It is important to note that chronic inflammation in asthma and other pulmonary diseases such as COPD mainly involves the infiltration of neutrophils, the major inflammatory cells enrolled in the process, into the small airways.

One possible mechanism of the anti-inflammatory action is that smooth muscle cells relaxation can reduce endothelial permeability, and consequently reduce the migration of blood inflammatory factors, decreasing the inflammatory process. Therefore, potent peptides in eliciting more potent vasodilatation, such as SEQ ID 24 and SEQ ID: 19, have more anti-inflammatory effect compared to PnT(x)19.

Incorporated-by-reference is the material (Sequence Listing) in the ASCII text file filed via EFS-Web under the Legal Framework:
Named: 2_248_$O_{028}$_Seq_Listing_ST25.txt
Created: Dec. 26, 2019, and
Size: 10,452 bytes.

What is claimed is:

1. A synthetic peptide, consisting of SEQ ID NO: 17, SEQ ID NO: 18, SEQ ID NO: 19, SEQ ID NO: 20, SEQ ID NO: 22, SEQ ID NO: 23, or SEQ ID NO: 24, wherein said synthetic peptide is a bronchodilator.

2. A pharmaceutical composition, comprising the synthetic peptide of claim 1 and a pharmaceutically acceptable excipient.

3. A synthetic peptide in the form of a multimer comprising two or more peptides selected from the group consisting of SEQ ID NO: 17, SEQ ID NO: 18, SEQ ID NO: 19, SEQ ID NO: 20, SEQ ID NO: 22, SEQ ID NO: 23 or SEQ ID NO: 24 wherein the peptide is interspaced by amino acid-based cleavable linkers.

4. A method of making a pharmaceutical composition, comprising combining a pharmaceutically acceptable excipient to the synthetic peptide of claim 1.

5. A method for treating a disorder in a patient in need of modulation of the tone of smooth muscle, comprising administering to the patient a therapeutically effective amount of the synthetic peptide of claim 1.

6. The method of claim 5, wherein the disorder is selected from the group consisting of benign prostatic hyperplasia (BPH), Raynaud's syndrome, pulmonary arterial hypertension (PAH), systemic arterial hypertension (SAH) and hyper-reactivity of the airways associated to asthma, COPD, pulmonary fibrosis, silicosis, allergic bronchopulmonary aspergillosis, hereditary angioedema, and neonatal hypoxemic respiratory failure.

7. The method of claim 5, wherein the disorder is pulmonary arterial hypertension (PAH).

8. A synthetic peptide comprising N- and C-terminal modifications, the peptide is selected from the group consisting of SEQ ID NO: 17, SEQ ID NO: 18, SEQ ID NO: 19, SEQ ID NO: 20, SEQ ID NO: 22, SEQ ID NO: 23, or SEQ ID NO: 24, wherein the N-terminal modification is selected from acetyl, chloride, or trifluoroacetyl covalently bonded to the N-terminus of the peptide; and the C-terminal modification is $NH_2$ covalently bonded to the C-terminus of the peptide.

9. The synthetic peptide of claim 8, wherein the peptide is further linked to a half-life enhancing moiety selected from the group consisting of albumin-binding moieties.

10. The synthetic peptide of claim 8, wherein the N-terminal modification is an acetyl covalently bonded to the N-terminus of the peptide.

11. A pharmaceutical composition, comprising the synthetic peptide of claim 8 and a pharmaceutically acceptable excipient.

12. A method of making a pharmaceutical composition, comprising combining a pharmaceutically acceptable excipient to the synthetic peptide of claim 8.

13. A method for treating a disorder in a patient in need of modulation of the tone of smooth muscle, comprising administering to the patient a therapeutically effective amount of the synthetic peptide of claim 8.

14. The method of claim 13, wherein the disorder is selected from the group consisting of benign prostatic hyperplasia (BPH), Raynaud's syndrome, pulmonary arterial hypertension (PAH), systemic arterial hypertension (SAH) and hyper-reactivity of the airways associated to asthma, COPD, pulmonary fibrosis, silicosis, allergic bronchopulmonary aspergillosis, hereditary angioedema, and neonatal hypoxemic respiratory failure.

15. The method of claim 13, wherein the disorder is pulmonary arterial hypertension (PAH).

* * * * *